United States Patent
Takahashi et al.

(10) Patent No.: US 7,593,652 B2
(45) Date of Patent: Sep. 22, 2009

(54) IMAGE FORMING APPARATUS AND IMAGE FORMING SYSTEM THAT CALCULATE OPERATION AMOUNT OF COMPONENTS THEREOF

(75) Inventors: Yutaka Takahashi, Tokyo (JP); Toshihiro Sugiyama, Tokyo (JP); Jun Shiori, Kanagawa (JP)

(73) Assignee: Ricoh Company, Limited, Tokyo (JP)

( * ) Notice: Subject to any disclaimer, the term of this patent is extended or adjusted under 35 U.S.C. 154(b) by 177 days.

(21) Appl. No.: 11/598,691

(22) Filed: Nov. 14, 2006

(65) Prior Publication Data

US 2007/0122166 A1    May 31, 2007

(30) Foreign Application Priority Data

Nov. 30, 2005   (JP)   ............................. 2005-346326

(51) Int. Cl.
G03G 15/00   (2006.01)
(52) U.S. Cl. ....................................................... 399/24
(58) Field of Classification Search .................. 399/24, 399/25, 27, 31, 34
See application file for complete search history.

(56) References Cited

U.S. PATENT DOCUMENTS

| 5,196,884 | A | | 3/1993 | Sugiyama et al. |
| 6,144,812 | A | * | 11/2000 | Ueno ........................... 399/12 |
| 2004/0091274 | A1 | * | 5/2004 | Saito et al. .................... 399/24 |
| 2006/0034626 | A1 | * | 2/2006 | Tanaka ......................... 399/12 |
| 2006/0062583 | A1 | * | 3/2006 | Kikuchi ........................ 399/24 |

FOREIGN PATENT DOCUMENTS

| JP | 09-146423 | 6/1997 |
| JP | 2003-076223 | 3/2003 |
| JP | 2005-257781 | 9/2005 |

* cited by examiner

*Primary Examiner*—Quana M Grainger
(74) *Attorney, Agent, or Firm*—Harness, Dickey & Pierce, P.L.C.

(57) ABSTRACT

Process units, a transfer unit, a belt cleaning unit, a secondary transfer unit and a fixing unit each include a storage unit that stores therein information on the operation amount thereof measured by a controller as operation record with respect to each unit. The controller updates the information stored in the storage unit after each time the controller measures the operation amount. The controller calculates remaining lifetime of the units based on the operation amount and a predetermined lifetime index.

12 Claims, 11 Drawing Sheets

IMAGE FORMING APPARATUS AND IMAGE FORMING SYSTEM THAT CALCULATE OPERATION AMOUNT OF COMPONENTS THEREOF

CROSS-REFERENCE TO RELATED APPLICATIONS

The present document incorporates by reference the entire contents of Japanese priority document, 2005-346326 filed in Japan on Nov. 30, 2005.

BACKGROUND OF THE INVENTION

1. Field of the Invention

The present invention relates to an image forming apparatus that includes a plurality of components and calculates an operation amount of each of the components, and an image forming system that includes the image forming apparatus.

2. Description of the Related Art

When a failure occurs in a part of various types of devices, depending on the type of the part, the device cannot be used until the part is replaced by a new one, and this imposes inconvenience on a user.

Japanese Patent Application Laid-open No. 2005-257781 discloses an image forming apparatus that calculates remaining lifetime of a fixing device based on the operation amount of the fixing device, and displays the remaining lifetime thus obtained on a display unit. The conventional image forming apparatus allows a user to determine whether the fixing device will be worn out soon based on the remaining lifetime displayed on the display unit. Accordingly, when the fixing device is likely to be worn out soon, it can be replaced before being worn out. Thus, downtime of the image forming apparatus due to a failure of the fixing device can be reduced.

In the conventional technology, however, replacement of a part or a component such as the fixing device is not always correctly performed. That is, if a user obtains a secondhand part of the image forming apparatus in some way, and a part of his/her image forming apparatus is likely to be worn out, the part can be replaced by not by a new one but the secondhand part. In this case, even if the part is has been used and deteriorated to some extent, the remaining lifetime thereafter is calculated as a new part. Consequently, it is determined that there is a sufficient time until the part is worn out when the part may be worn out soon.

SUMMARY OF THE INVENTION

It is an object of the present invention to at least partially solve the problems in the conventional technology.

According to an aspect of the present invention, an image forming apparatus includes an image forming unit that forms an image on a recording medium, and includes a component held in a holding unit, and a measuring unit that measures an operation amount of the component. Any one of the component and the holding unit includes a storage unit that stores therein operation amount information on the operation amount obtained by the measuring unit, and the measuring unit updates the operation amount information after measuring the operation amount.

According to another aspect of the present invention, an image forming system includes an image forming unit and a lifetime management unit. The image forming unit forms an image on a recording medium and includes a component held in a holding unit. The lifetime management unit includes a measuring unit that measures an operation amount of the component, and a calculating unit that calculates a remaining lifetime of the component based on the operation amount and a lifetime index. Any one of the component and the holding unit includes a storage unit that stores therein operation amount information on the operation amount obtained by the measuring unit, and the measuring unit updates the operation amount information after measuring the operation amount.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained below with reference to the accompanying drawings. In the embodiments, the present invention is applied to an image forming system that includes an electrophotographic printer (hereinafter, "printer").

Figure 1:
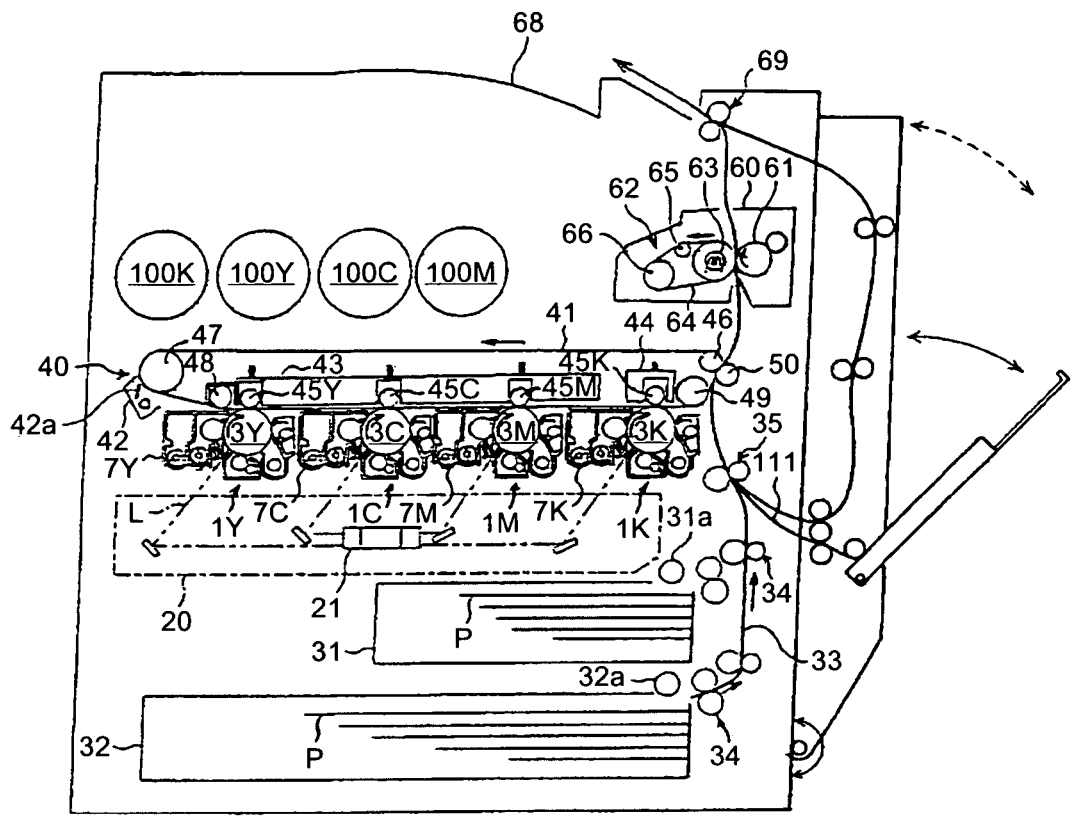
FIG. 1 is a schematic of a printer in an image forming system according to an embodiment of the present invention.
Figure 2:
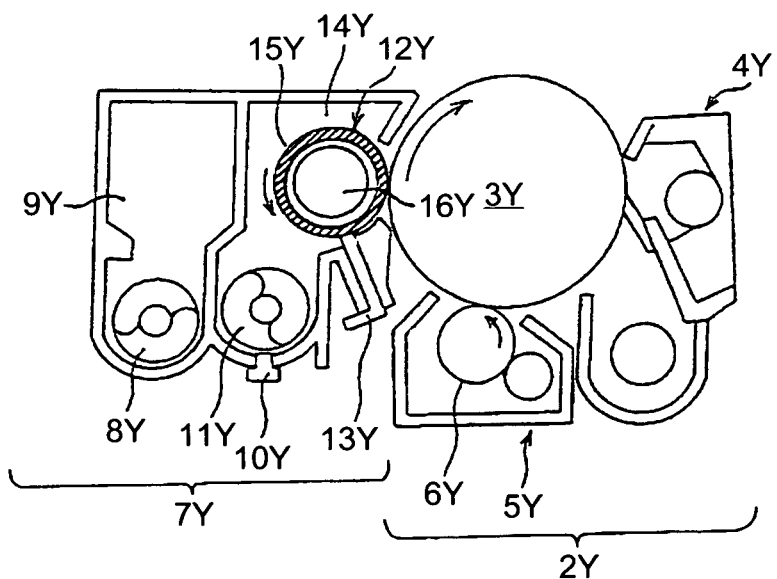
FIG. 2 is an enlarged view of a yellow (Y) process unit of the printer.
Figure 3:
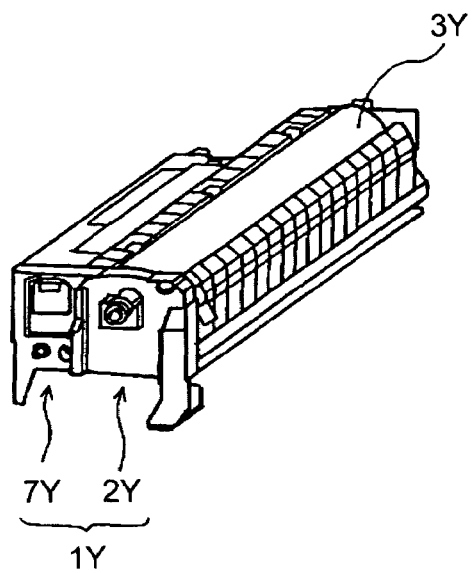
FIG. 3 is a perspective view of the process unit.
Figure 4:
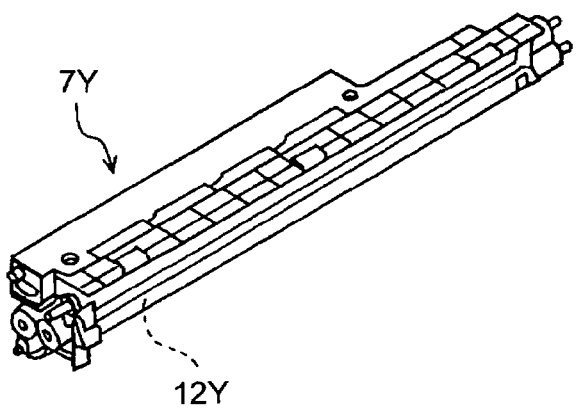
FIG. 4 is a perspective view of a developing unit in the process unit.

A basic configuration of a printer as an image forming apparatus of an image forming system according to an embodiment is explained first referring to FIG. 1. The printer includes four process units 1Y, 1C, 1M, and 1K that form toner images of yellow, magenta, cyan, and black (hereinafter, "Y, C, M, and K"). The process units 1Y, 1C, 1M, and 1K have the same configuration except that they use toner of different colors Y, C, M, and K to form an image. FIG. 2 is an enlarged view of the process unit 1Y for forming a Y toner image. The process unit 1Y includes a photoconductor unit 2Y and a developing unit 7Y. As shown in FIG. 3, the photoconductor unit 2Y and the developing unit 7Y are detachably mounted on the printer to be integrated into the process unit 1Y. When detached from the printer, as shown in FIG. 4, the developing unit 7Y can be attached to and detached from the photoconductor unit 2Y.

The photoconductor unit 2Y includes a photosensitive drum 3Y as a latent image carrier, a drum cleaning unit 4Y, a discharger (not shown), a charger 5Y.

FIG. 2 depicts the charger 5Y that uniformly charges a surface of the photosensitive drum 3Y rotated clockwise in FIG. 2 by a drive unit (not shown). The charger 5Y uniformly charges the photosensitive drum 3Y by moving a charging roller 6Y rotated counterclockwise in FIG. 2 close to the photosensitive drum 3Y, while a charging bias is being applied thereto by a power source (not shown). Instead of the charging roller 6Y, a charger can also be used in which a charging brush contacts the photosensitive drum 3Y. Further, a charger can also be used which uniformly charges the photosensitive drum 3Y in the same manner as a scorotron charger. The surface of the photosensitive drum 3Y uniformly charged by the charger 5Y is exposed and scanned by a laser beam emitted from an optical writing unit, thereby carrying a Y electrostatic latent image.

The developing unit 7Y includes a first developer container 9Y including a first screw 8Y therein. The developing unit 7Y further includes a second developer container 14Y including a density sensor consisting of a permeability sensor (hereinafter, density sensor) 10Y, a second screw 11Y, a developing roller 12Y, and a doctor blade 13Y. The first and second developer containers contain a Y developer (not shown) including a magnetic carrier and a negatively charged Y toner. The first screw 8Y is rotated by the drive unit (not shown) to convey the Y developer in the first developer container 9Y from front to back in a direction perpendicular to the drawing. The Y developer passes through an opening (not shown) on a partition between the first and second developer containers 9Y and 14Y to enter the second developer container 14Y.

The second screw 11Y in the second developer container 14Y is rotated by the drive unit (not shown) to transport the Y developer from back to front in FIG. 2. The toner density of the Y developer being transported is detected by the density sensor 10Y fixed on the bottom of the second developer container 14Y. In FIG. 2, above the second screw 11Y that transports the Y developer is arranged the developing roller 12Y in parallel to the second screw 11Y. The developing roller 12Y includes a magnet roller 16Y in a developing sleeve 15Y formed of a non-magnetic pipe rotated counterclockwise in FIG. 2. A part of the Y developer transported by the second screw 11Y is drawn onto the surface of the developing sleeve 15Y by a magnetic force of the magnet roller 16Y. A film thickness thereof is regulated by the doctor blade 13Y arranged to hold a predetermined gap between the developing sleeve 15Y and the doctor blade 13Y. The Y developer is then transported to a developing area opposite to the photosensitive drum 3Y, so that the Y toner is adhered to the Y electrostatic latent image on the photosensitive drum 3Y. The Y developer with the Y toner being consumed due to development is returned onto the second screw 11Y with the rotation of the developing sleeve 15Y of the developing roller 12Y. When the Y developer is transported to the front side in FIG. 2, the Y developer is returned to the first developer container 9Y via the opening (not shown).

A permeability detection result of the Y developer by the density sensor 10Y is sent to a controller (not shown) as a voltage signal. The permeability of the Y developer correlates with the Y toner density of the Y developer, and the density sensor 10Y outputs a voltage of a value corresponding to the Y toner density. The controller includes a random access memory (RAM), which stores Y Vtref, i.e., a target value of an output voltage from the density sensor 10Y, and data of C Vtref, M Vtref, and K Vtref, i.e., target values of the output voltage from the C, M, and K density sensors mounted on other developing units 7C, 7M, and 7K. The developing unit 7Y compares a value of the output voltage from the density sensor 10Y with the Y Vtref, and drives a Y toner supply unit for time corresponding to the comparison result. Due to this drive, an adequate amount of Y toner is supplied to the Y developer, in which the Y toner has been consumed due to development and the toner density has decreased, by the first developer container 9Y. Accordingly, the Y toner density of the Y developer in the second developer container 14Y is maintained in a predetermined range. The same toner supply control is performed with respect to the developer in the process units (1C, 1M, 1K) for other colors.

The Y toner image formed on the photosensitive drum 3Y is intermediately transferred onto an intermediate transfer belt. The drum cleaning unit 4Y in the photoconductor unit 2Y removes remaining toner on the surface of the photosensitive drum 3Y, having subjected to the intermediate transfer process. The surface of the photosensitive drum 3Y having subjected to the cleaning process is discharged by the discharger (not shown). Due to the discharge, the surface of the photosensitive drum 3Y is initialized and prepared for the next image formation. In FIG. 1, also in the process units 1C, 1M, and 1K for other colors, the C, M, and K toner image is formed on the photosensitive drum 3C, 3M, and 3K, respectively, in the same manner and intermediately transferred onto the intermediate transfer belt.

An optical write unit 20 is arranged below the process units 1Y, 1C, 1M, and 1K in FIG. 1. The optical write unit 20 as a latent image forming unit irradiates a laser beam L emitted based on the image information onto the photosensitive drums 3Y, 3C, 3M, and 3K of the respective process units 1Y, 1C, 1M, and 1K. Accordingly, Y, C, M, and K electrostatic latent images are formed respectively on the photosensitive drums 3Y, 3C, 3M, and 3K. The optical write unit 20 irradiates the laser beam L emitted from the light source via a plurality of optical lenses and mirrors, while deflecting the laser beam by a polygon mirror 21 rotated by a motor. Instead of this configuration, an optical write unit that performs optical scan by light-emitting diode (LED) arrays can be employed.

A first paper feed cassette 31 and a second paper feed cassette 32 are arranged below the optical write unit 20 to be overlapped on each other in a vertical direction. Recording paper P is stored in these paper feed cassettes in a state of paper stack in which plural sheets of the recording paper are piled, and a first paper feed roller 31a and a second paper feed roller 32a contact the top sheet of the recording paper P. When the first paper feed roller 31a is rotated counterclockwise in FIG. 1 by a drive unit (not shown), the top sheet of the recording paper P in the first paper feed cassette 31 is discharged toward a paper feed path 33 arranged to extend in the vertical direction on the right of the cassette in FIG. 1. Further, when the second paper feed roller 32a is rotated counterclockwise in FIG. 1 by the drive unit (not shown), the top sheet of the recording paper P in the second paper feed cassette 32 is discharged toward the paper feed path 33. In the paper feed path 33, a plurality of carrier roller pairs 34 is arranged, so that the recording paper P fed to the paper feed path 33 is put between the rollers of the carrier roller pairs 34 and carried from the lower part to the upper part in FIG. 1 in the paper feed path 33.

A resist roller pair 35 is arranged at the end of the paper feed path 33. Upon insertion of the recording paper P fed from the carrier roller pair 34 between the rollers, the resist roller pair 35 temporarily stops the rotation of the rollers. The recording paper P is then fed to a secondary transfer nip (described later) at an appropriate timing.

Above the process units 1Y, 1C, 1M, and 1K is arranged a transfer unit 40 that endlessly moves an intermediate transfer belt 41 counterclockwise in FIG. 1, while extending the intermediate transfer-belt 41. The transfer unit 40 includes a belt cleaning unit 42, a first bracket 43, and a second bracket 44 in addition to the intermediate transfer belt 41. The transfer unit 40 further includes four primary transfer rollers 45Y, 45C, 45M, and 45K, a secondary transfer backup roller 46, a drive roller 47, a supplementary roller 48, and a tension roller 49. The intermediate transfer belt 41 is endlessly moved counterclockwise in FIG. 1 due to rotation of the drive roller 47, while being extended over eight rollers. The four primary transfer rollers 45Y, 45C, 45M, and 45K put the endlessly moved intermediate transfer belt 41 between the photosensitive drums 3Y, 3C, 3M, and 3K and the primary transfer rollers to form a primary transfer nip. The primary transfer rollers 45Y, 45C, 45M, and 45K then apply a transfer bias of a polarity (for example, positive) opposite to that of the toner to a back face (internal circumference of a loop) of the intermediate transfer belt 41. While the intermediate transfer belt 41 sequentially passes the primary transfer nips for Y, C, M, and K with the endless movement, the Y, C, M, and K toner images on the photosensitive drums 3Y, 3C, 3M, and 3K are superposed and primarily transferred on a front face thereof. Accordingly, a four-color-superposed toner image (hereinafter, "four-color toner image") is formed on the intermediate transfer belt 41.

The secondary transfer backup roller 46 puts the intermediate transfer belt 41 between a secondary transfer roller 50 arranged outside of the loop of the intermediate transfer belt 41 and the secondary transfer backup roller 46, to form a secondary transfer nip. The resist roller pair 35 forwards the recording paper P put between the rollers toward the secondary transfer nip at a timing synchronized with the four-color toner image on the intermediate transfer belt 41. The four-color toner image on the intermediate transfer belt 41 is secondarily batch-transferred onto the recording paper P in the secondary transfer nip, due to an influence of a secondary transfer field formed between the secondary transfer roller 50 and the secondary transfer backup roller 46, to which a secondary transfer bias is applied, and a nip pressure. The four-color toner image becomes a full color toner image, coupled with white of the recording paper P.

Residual toner, which has not been transferred to the recording paper P, adheres on the intermediate transfer belt 41 after having passed through the secondary transfer nip. The residual toner is cleaned by the belt cleaning unit 42. In the belt cleaning unit 42, a cleaning blade 42a contacts the front face of the intermediate transfer belt 41, thereby scraping and removing the residual toner on the belt.

Figure 5:
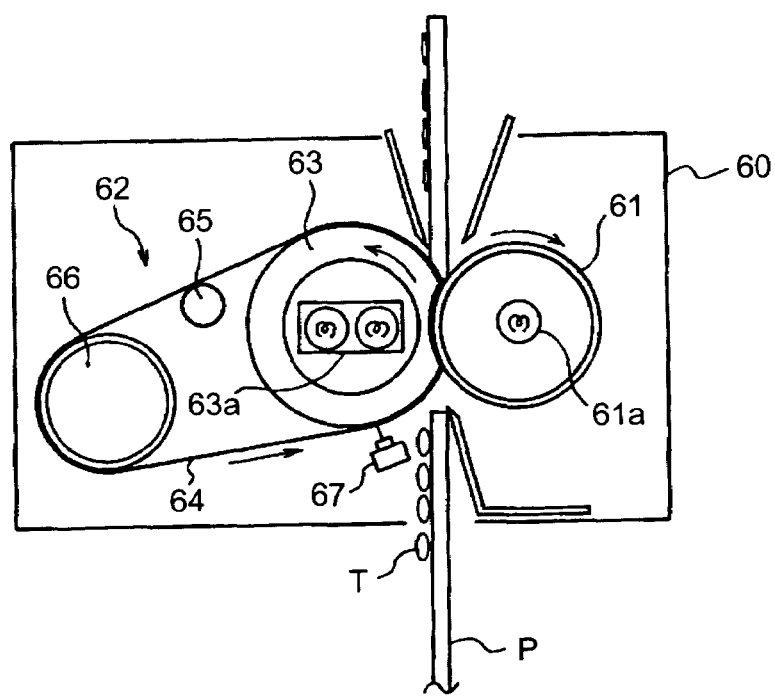
FIG. 5 is an enlarged view of a fixing unit of the printer.

A fixing unit 60 is arranged above the secondary transfer nip in FIG. 1. As shown in FIG. 5, the fixing unit 60 includes a pressurizing heating roller 61 that contains a heat source 61a such as a halogen lamp, and a fixing belt unit 62. The fixing belt unit 62 includes a fixing belt 64, a heating roller 63 including a heat source 63a such as a halogen lamp, a tension roller 65, a drive roller 66, and a temperature sensor 67. The fixing belt unit 62 endlessly moves the endless fixing belt 64 counterclockwise in FIG. 5, while extending the fixing belt 64 across the heating roller 63, the tension roller 65, and the drive roller 66. In the process of endless movement, the fixing belt 64 is heated from a backside by the heating roller 63. The pressurizing heating roller 61 rotated clockwise in FIG. 5 contacts a position where the fixing belt 64 heated in this manner is spanned over the heating roller 63 from the front face side. Accordingly, a fixing nip is formed, where the pressurizing heating roller 61 and the fixing belt 64 contact each other.

The temperature sensor 67 is arranged to face the front face of the fixing belt 64 via a predetermined gap, outside of the loop of the fixing belt 64, and detects a surface temperature of the fixing belt 64 immediately before approaching the fixing nip. The detection result is transmitted to a fixing power source circuit (not shown). The fixing power source circuit controls on/off of power supply relative to the heat source 63a contained in the heating roller 63 and the heat source 61a contained in the pressurizing heating roller 61. Accordingly, the surface temperature of the fixing belt 64 is maintained at about 140 degrees.

In FIG. 1, the recording paper P having passed through the secondary transfer nip is separated from the intermediate transfer belt 41, and forwarded into the fixing unit 60. During a process of transport from the lower part to the upper part in FIG. 1, while being put between the fixing nip in the fixing unit 60, the recording paper P is heated and pressed by the fixing belt 64, thereby fixing the full color toner image.

The recording paper P having subjected to the fixing process in this manner passes through the rollers of a paper ejection roller pair 69 and ejected to the outside of the machine. A stack unit 68 is formed on the upper face of the housing of the printer, and the recording paper P ejected to the outside of the machine by the paper ejection roller pair 69 is sequentially stacked in the stack unit 68.

Four toner cartridges 100Y, 100C, 100M, and 100K for storing the Y, C, M, and K toners are arranged above the transfer unit 40. The Y, C, M, and K toners in the toner cartridges 100Y, 100C, 100M, and 100K are appropriately supplied to the developing units 7Y, 7C, 7M, and 7K in the process units 1Y, 1C, 1M, and 1K. These toner cartridges 100Y, 100C, 100M, and 100K can be attached to or detached from the printer, separately from the process units 1Y, 1C, 1M, and 1K.

Figure 6:
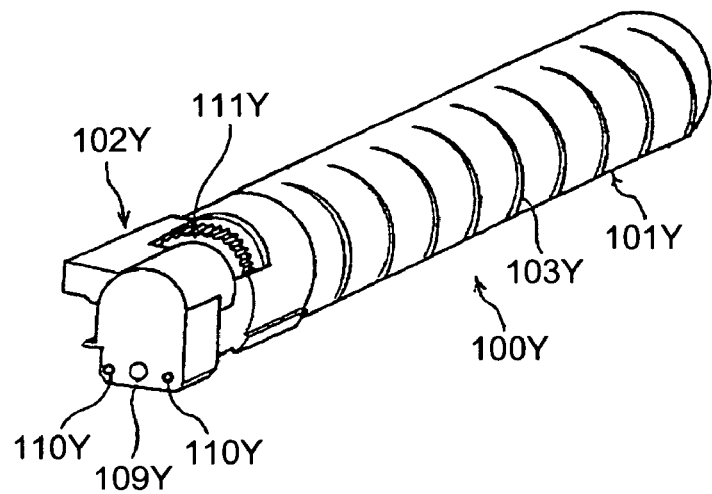
FIG. 6 is a perspective view of a Y toner cartridge in the printer.

FIG. 6 is a perspective view of the toner cartridge 100Y. The toner cartridge 100Y includes a bottle part 101Y for storing the Y toner (not shown), and a cylindrical holder part 102Y. The holder part 102Y rotatably holds the bottle part 101Y, while engaging with a point of the bottle part 101Y to cover an opening (not shown) formed at the point of the bottle part 101Y. On the bottle part 101Y, screw-shape protrusions 103Y protruding from outside toward inside are embossed along the internal circumference thereof. When the bottle part 101Y is driven by a drive system (not shown), the Y toner in the bottle part 101Y moves from the bottom side of the bottle toward the point side of the bottle along the screw-shape protrusions, and flows into the cylindrical holder part 102Y, through the opening (not shown) provided at the point of the bottle part 101Y, which is a toner container.

A nozzle receiving port 109Y is formed at the end of the holder part 102Y in a bottle axial direction. The nozzle receiving port 109Y is for receiving a suction nozzle fixed on the printer side. Pin receiving ports 110Y having a slightly smaller diameter than that of the nozzle receiving port are formed on both sides of the nozzle receiving port 109Y in FIG. 6. The pin receiving ports 110Y are formed, respectively, at positions deviated from a rotation axis of the bottle part 101Y, and a pin insertion path (not shown) is formed in the inner side thereof to extend in a direction parallel to the rotation axis of the bottle part 101Y. As the bottle part 101Y, a resin material having a high rigidity so as not to be deformed by an impact at the time of rotation by a drive transmission gear is used.

Figure 7:
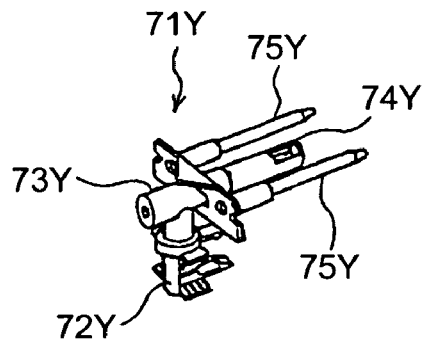
FIG. 7 is a perspective view of a cartridge connecting portion, which is a part of a toner supply unit of the printer.

FIG. 7 is a perspective view of a cartridge connecting portion 71Y, which is a part of a toner supply unit. The cartridge connecting portion 71Y is fixed at the upper end of a flow tube 72Y for allowing the Y toner to flow, so that a suction nozzle 73Y extends in a horizontal direction. At the end of the suction nozzle 73Y, a toner receiving port 74Y is formed to receive the Y toner. Bar-shaped positioning pins 75Y are fixed on both sides of the suction nozzle 73Y to extend in the horizontal direction (in a direction parallel to the rotation axis of the bottle part). The positioning pins 75Y, which are protrusions of the cartridge connecting portion 71Y as a positioning member, protrude over the end of the suction nozzle 73Y.

When the toner cartridge 100Y is to be set on a cartridge mounting base of the toner supply unit, at first, an opening/closing door (not shown) on a side of the printer is opened so that the cartridge mounting base in the toner supply unit is exposed. On the cartridge mounting base, four depressions in a semi-cylindrical shape are provided in parallel, for mounting four toner cartridges for Y. C, M, and K in parallel. An operator holds the toner cartridge 100Y with the holder part 102Y directed to the front. The operator then puts the holder part 102Y at the end of a depression for Y, of four semi-cylindrical depressions provided on the cartridge mounting base, and slides the cartridge along the rotation axis of the bottle part to insert the entire cartridge. The operator pushes the toner cartridge 100Y to a predetermined position by this sliding movement, and sets the toner cartridge 100Y on the cartridge mounting base.

The two positioning pins 75Y in the cartridge connecting portion 71Y in the toner supply unit are fixed such that the point thereof protrudes than the point of the suction nozzle 73Y. The point thereof is more tapered than the rear end. During the insertion of the toner cartridge in the cartridge mounting base at the time of setting the toner cartridge, the tapered points of the two positioning pins 75Y respectively enter into the two pin receiving ports 110Y of the toner cartridge 100Y shown in FIG. 6. When the toner cartridge 100Y is further inserted, the rear ends of the positioning pins 75Y thicker than the point thereof also enter into the pin receiving port 110Y, thereby positioning the toner cartridge 100Y in a direction orthogonal to the rotation axis on the cartridge mounting base.

After such positioning is performed, when the toner cartridge 100Y is further inserted, the suction nozzle 73Y in the cartridge connecting portion 71Y enters into the nozzle receiving port 109Y in the holder part 102Y. Setting of the toner cartridge 100Y is complete at a point in time when the suction nozzle 73Y is pushed into an insertion path (115Y) extending inside of the nozzle receiving port 109Y.

The thus set toner cartridge 100Y makes a gear portion 111Y formed at the point of the bottle part 101Y engage with the drive transmission gear (not shown) fixed in the toner supply unit. When the drive transmission gear is rotated, the bottle part 101Y rotates, while being held by the holder part 102Y. Due to this rotation, the Y toner in the bottle part 101Y is carried from the rear end toward the point of the bottle, and flows into the holder part 102Y.

The suction pump is connected to an area (not shown) of the flow tube 72Y connected to the suction nozzle 73Y, and air and the toner in the flow tube 72Y are sucked due to the operation thereof. The suction force is transmitted to the holder part 102Y through the flow tube 72Y and the suction nozzle 73Y. The Y toner in the holder part 102Y is then sucked into the suction nozzle 73Y, and supplied to the developing unit 7Y in the process unit 1Y.

While the toner cartridge 100Y for storing the Y toner has been explained in detail, the toner cartridges for other colors (100C, 100M, and 100K) have the same configuration.

Figure 8:
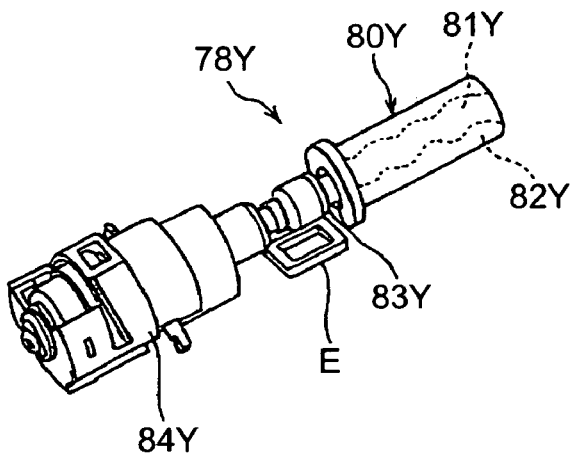
FIG. 8 is a perspective view of a Y suction pump of four suction pumps in the toner supply unit.

FIG. 8 is a perspective view of a suction pump 78Y of four suction pumps in the toner supply unit. The suction pump 78Y is of a type referred to as uniaxial eccentric screw pump (generally called as monopump). A pump part 80Y is formed of a rotor 81Y machined in an eccentric double screw shape from a metal or a resin having high rigidity, a stator 82Y in which a double screw-shape cavity is formed in a material of rubber or the like, and a resin holder for containing these rotor and stator. The suction pump 78Y also includes a discharge part 83Y, and a motor 84Y for rotating the rotor 81Y, in addition to the pump part 80Y. When the double screw-shape rotor 81Y rotates in the stator 82Y, a negative pressure is generated on the suction side (the right side in FIG. 8) of the pump part 80Y. Due to the negative pressure, the Y toner in the toner cartridge 100Y is sucked via the flow tube 72Y and the like. The Y toner reaches the pump part 80Y of the suction pump 78Y, passes through the stator 82Y, and is discharged from the discharge part 83Y. Suction pumps for other colors have the same configuration.

Figure 9:
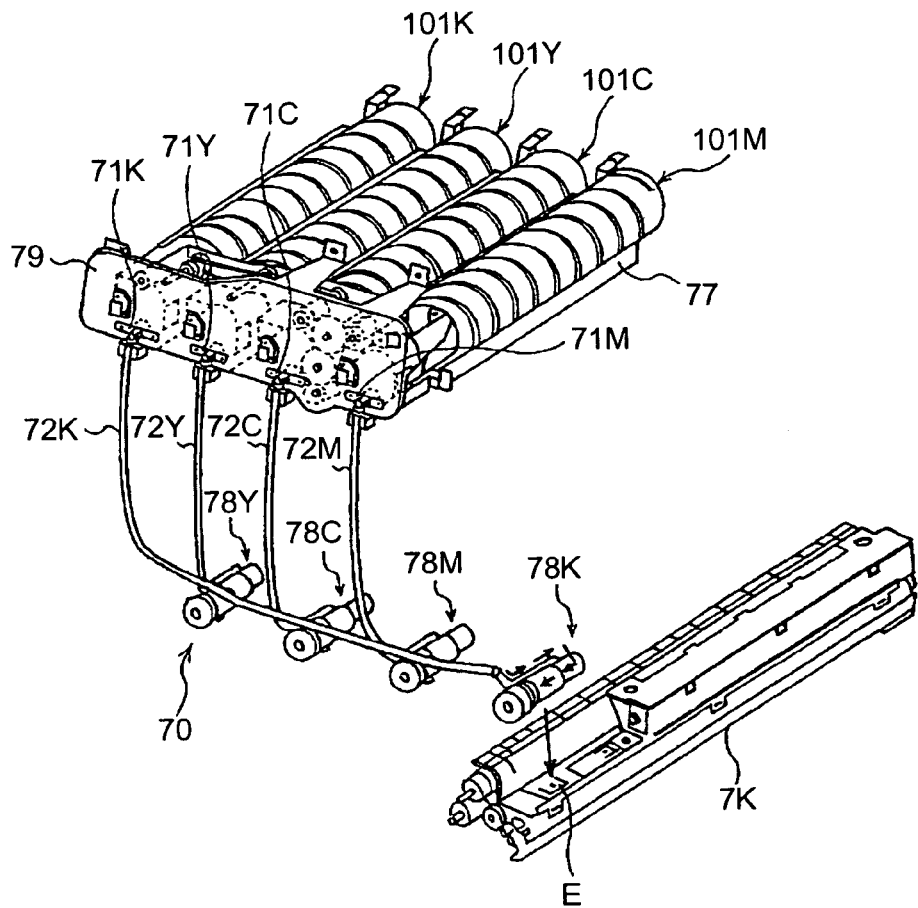
FIG. 9 is a perspective view of the toner supply unit and a peripheral configuration thereof.

FIG. 9 is a perspective view of a toner supply unit 70 and a peripheral configuration thereof. The toner supply unit 70 includes a cartridge mounting base 77, four cartridge connecting portions 71Y, 71C, 71M, and 71K, and four suction pumps 78Y, 78C, 78M, and 78K. The cartridge mounting base 77 includes four semi-cylindrical depressions for mounting the four toner cartridges 100Y, 100C, 100M, and 100K parallel with each other. The transfer unit (not shown) is arranged below the cartridge mounting base 77, and the four developing units are arranged further below. In FIG. 9, only the developing unit 7K is shown of the four developing units for simplicity.

On the side of the printer housing (not shown), the opening/closing door for replacing the cartridge is provided, and when this door is opened, the toner supply unit 70 in the housing is exposed on the inner side of FIG. 9. The operator pushes the toner cartridges 100Y, 100C, 100M, and 100K in a longitudinal direction of the bottle to slide the cartridges on the cartridge mounting base 77, thereby setting the cartridges in the toner supply unit 70.

A connecting unit support plate 79 for supporting the four cartridge connecting portions 71Y, 71C, 71M, and 71K is arranged in a standing condition at one end of the cartridge mounting base 77. The suction nozzles of the cartridge connecting portions 71Y, 71C, 71M, and 71K are respectively inserted into a nozzle insertion passage (not shown) in the toner cartridges 100Y, 100C, 100M, and 100K mounted on the cartridge mounting base 77. The suction pumps 78Y, 78C, 78M, and 78K are coupled to the end of flow tubes 72Y, 72C, 72M, and 72K of the cartridge connecting portions 71Y, 71C, 71M, and 71K. A toner supply port E of each developing unit is positioned immediately below the respective suction pumps 78Y, 78C, 78M, and 78K. The Y, C, M, and K toners respectively discharged from the discharge part of the suction pumps 78Y, 78C, 78M, and 78K are supplied to the inside of the developing unit via the toner supply port of the corresponding developing unit. In FIG. 9, while only the developing unit 7K is shown, the developing units 7Y, 7M, and 7C are respectively positioned immediately below the suction pumps 78Y, 78M, and 78C.

Figure 10:
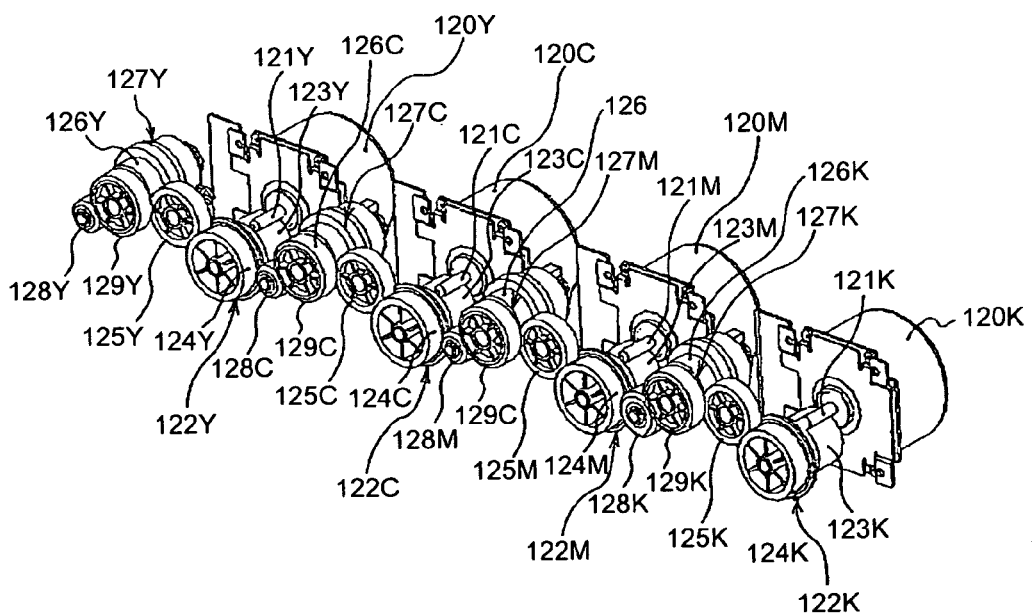
FIG. 10 is a perspective view of a drive transmission unit, which is a drive transmission system fixed in the printer.
Figure 11:
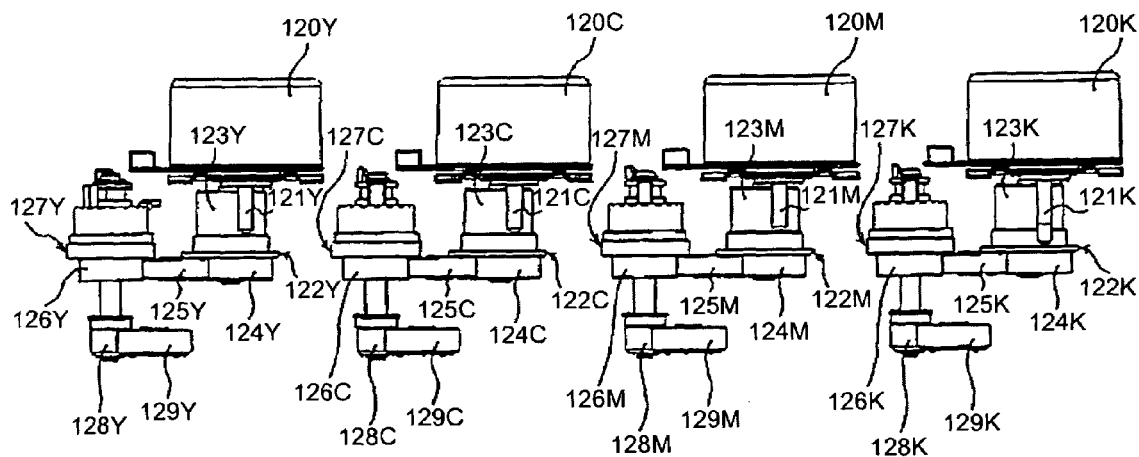
FIG. 11 is an overhead plan view of the drive transmission unit.

FIG. 10 is a perspective view of a drive transmission unit on the body side, which is a drive transmission system fixed in the printer. FIG. 11 is an overhead plan view of the drive transmission unit. The support plate is arranged in a standing condition in the printer housing, and four process drive motors 120Y, 120C, 120M, and 120K are fixed thereto. Drive gears 121Y, 121C, 121M, and 121K are respectively fixed to a rotation shaft of the process drive motors 120Y, 120C, 120M, and 120K. Developing gears 122Y, 122C, 122M, and 122K that can slide and rotate, while engaging with a fixed shaft (not shown) provided in a protruding condition on the support plate, are arranged below the rotation shafts of the process drive motors 120Y, 120C, 120M, and 120K. The developing gears 122Y, 122C, 122M, and 122K respectively include first gears 123Y, 123C, 123M and 123K and second gears 124Y, 124C, 124M and 124K, which rotate on the same rotation shaft. The second gears 124Y, 124C, 124M, and 124K are positioned on the point side of the rotation shaft of the process drive motors 120Y, 120C, 120M, and 120K than the first gears 123Y, 123C, 123M, and 123K. The developing gears 122Y, 122C, 122M, and 122K slide and rotate on the fixed shaft due to the rotation of the process drive motors 120Y, 120C, 120M, and 120K, while engaging the first gears 123Y, 123C, 123M, and 123K with the drive gears 121Y, 121C, 121M, and 121K of the process drive motors 120Y, 120C, 120M, and 120K.

On the left side of the developing gears 122Y, 122C, 122M, and 122K, first relay gears 125Y, 125C, 125M, and 125K that slide and rotate while engaging with the fixed shaft (not shown) are arranged. These relay gears respectively engage with the second gears 124Y, 124C, 124M, and 124K of the developing gears 122Y, 122C, 122M, and 122K, and slide and rotate on the fixed shaft due to a rotation driving force from the developing gears 122Y, 122C, 122M, and 122K. The first relay gears 125Y, 125C, 125M, and 125K not only engage with the second gears 124Y, 124C, 124M, and 124K on a upstream side of a drive transmission direction, but also engage with clutch input gears 126Y, 126C, 126M, and 126K on a downstream side of the drive transmission direction. These clutch input gears 126Y, 126C, 126M, and 126K are respectively supported by developing clutches 127Y, 127C, 127M, and 127K. The developing clutches 127Y, 127C, 127M, and 127K transmit the rotation driving force to respective clutch shafts of the clutch input gears 126Y, 126C, 126M, and 126K, or make the clutch input gears 126Y, 126C, 126M, and 126K run idle, with on/off control of power supply by the controller (not shown). Clutch output gears 128Y, 128C, 128M, and 128K are respectively fixed on the point side of the clutch shafts of the developing clutches 127Y, 127C, 127M, and 127K. When the power is supplied to the developing clutches 127Y, 127C, 127M, and 127K, the rotation driving force of the clutch input gears 126Y, 126C, 126M, and 126K is transmitted to the clutch shafts, to rotate the clutch output gears 128Y, 128C, 128M, and 128K, respectively. On the other hand, when the power supply to the developing clutches 127Y, 127C, 127M, and 127K is cut off, even if the process drive motors 120Y, 120C, 120M, and 120K are rotating, since the clutch input gears 126Y, 126C, 126M, and 126K run idle on the clutch shafts, the rotation of the clutch output gears 128Y, 128C, 128M, and 128K stops.

Referring to FIG. 11, on the left side of the clutch output gears 128Y, 128C, 128M, and 128K, second relay gears 129Y, 129C, 129M, and 129K that can slide and rotate while engaging with the fixed shaft (not shown) are arranged, and rotate while engaging with the clutch output gears 128Y, 128C, 128M, and 128K.

On the printer, the following drive transmission system is configured to correspond to the four process units. That is, the drive transmission system includes the process drive motor 120, the drive gear 121, the first gear 123 and the second gear 124 of the developing gear 122, the first relay gear 125, the clutch input gear 126, the clutch output gear 128, and the second relay gear 129, and the driving rotation force is transmitted in this order.

Figure 12:
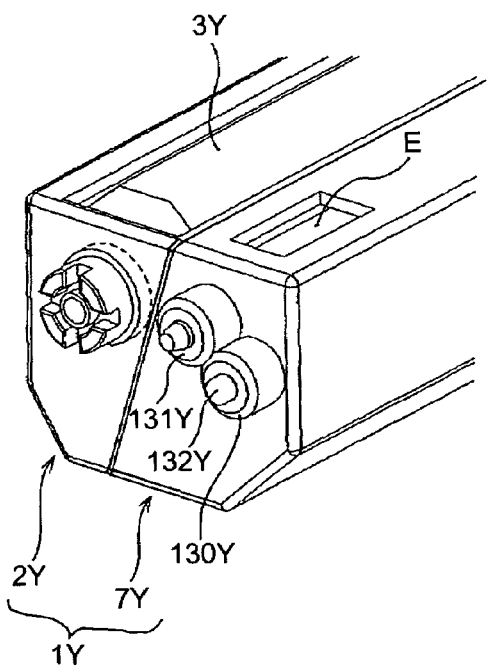
FIG. 12 is a partial perspective view of one end of the Y process unit.

FIG. 12 is a partial perspective view of one end of the process unit 1Y. A shaft member of the developing sleeve 15Y in a casing of the developing unit 7Y penetrates the side of the casing and protrudes to the outside. A sleeve upstream gear 131Y is fixed to the protruding shaft member. A fixed shaft 132Y is provided in a protruding condition on the side of the casing, and a third relay gear 130Y engages with the sleeve upstream gear 131Y, while engaging slidably and rotatably with the fixed shaft 132Y.

In a state that the process unit 1Y is set on the printer, the second relay gear 129Y shown in FIGS. 10 and 11 engages with the third relay gear 130Y, in addition to the sleeve upstream gear 131Y. The rotation driving force of the second relay gear 129Y is sequentially transmitted to the third relay gear 130Y and the sleeve upstream gear 131Y, thereby rotate the developing sleeve 15Y.

While only the process unit 1Y has been explained with reference to the drawings, also in the process units for other colors, the rotation driving force is transmitted to the developing sleeve in the same manner.

In FIG. 12, while only the one end of the process unit 1Y is shown, the shaft member at the other end of the developing sleeve 15Y penetrates the side of the casing at the other end and protrudes to the outside, and a sleeve downstream gear (not shown) is fixed to the protruding portion. The first screw 8Y and the second screw 11Y shown in FIG. 2 also allow the shaft member thereof to penetrate the side of the casing at the other end, and a first screw gear and a second screw gear (not shown) are fixed to the protruding portion. When the developing sleeve 15Y rotates due to transmission of driving force of the sleeve upstream gear 131Y, the sleeve downstream gear rotates at the other end. Accompanying this rotation, the second screw 11Y that receives the driving force with the second screw gear engaging with the sleeve downstream gear rotates, and the first screw 8Y that receives the driving force with the first screw gear engaging with the second screw gear also rotates. The process units for other colors have the same configuration.

Thus, four developing gear groups, each consisting of the drive gear 121, the developing gear 122, the first relay gear 125, the clutch input gear 126, the clutch output gear 128, the second relay gear 129, the third relay gear 130, the sleeve upstream gear 131, the sleeve downstream gear, the second screw gear, and the first screw gear, are formed correspondingly to the process units.

Figure 13:
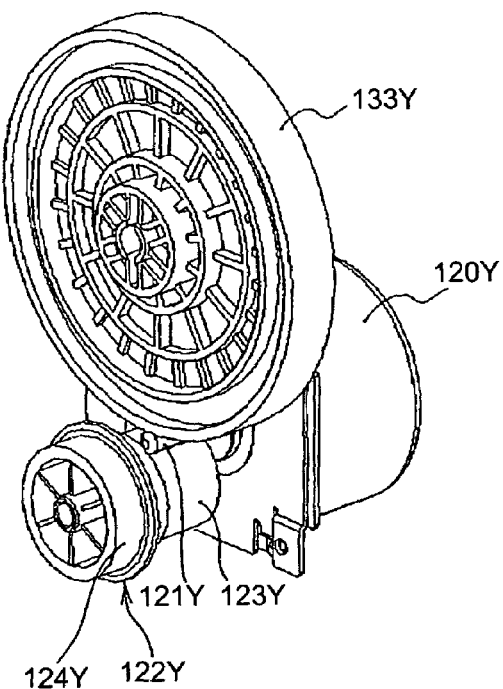
FIG. 13 is a perspective view of a Y photoconductor gear in the printer and a peripheral configuration thereof.

FIG. 13 is a perspective view of a photoconductor gear 133Y and a peripheral configuration thereof. The drive gear 121Y engages with the photoconductor gear 133Y as a latent image gear, in addition to the first gear 123Y of the developing gear 122Y. The photoconductor gear 133Y is fixed to a rotation shaft in a Y photosensitive drum (not shown), to form a part of the Y process unit. A diameter of the photoconductor gear 133Y is larger than that of the photosensitive drum. When the process drive motor 120Y rotates, the rotation driving force thereof is transmitted from the drive gear 121Y to the photoconductor gear by single-reduction gearing, thereby rotating the photosensitive drum. The process units for other colors have the same configuration. Thus, the printer in the image forming system includes four gear groups, each consisting of the drive gear 121 and the photoconductor gear 133, corresponding to the process units.

In FIG. 1, the first bracket 43 in the transfer unit 40 swings at a predetermined angle of rotation, centering on the rotation axis of the supplementary roller 48, with drive on/off of a solenoid (not shown). When forming a monochrome image, the printer of the image forming system slightly rotates the first bracket 43 counterclockwise in FIG. 1 by driving the solenoid. Due to this rotation, the primary transfer rollers 45Y, 45C, and 45M revolve counterclockwise, so that the intermediate transfer belt 41 is separated from the photosensitive drums 3Y, 3C, and 3M. Only the process unit 1K of the four process units 1Y, 1C, 1M, and 1K is driven to form a monochrome image. Accordingly, at the time of forming the monochrome image, wear of the process units due to useless driving of the process units 1Y, 1C, and 1M can be prevented.

In each color, the developing gear can be driven by a developing motor different from that of the photoconductor gear. In this case, a driven distance D of the developing unit (i=5 to 8) can be calculated based on the operating time of the developing motor.

In the printer having the above basic configuration, an image forming unit that forms an image on the recording paper P as the recording medium is configured by a combination of the process units 1Y, 1C, 1M, and 1K, the transfer unit 40, the belt cleaning unit 42, the secondary transfer unit include the secondary transfer roller 50, and the fixing unit 60.

Figure 14:
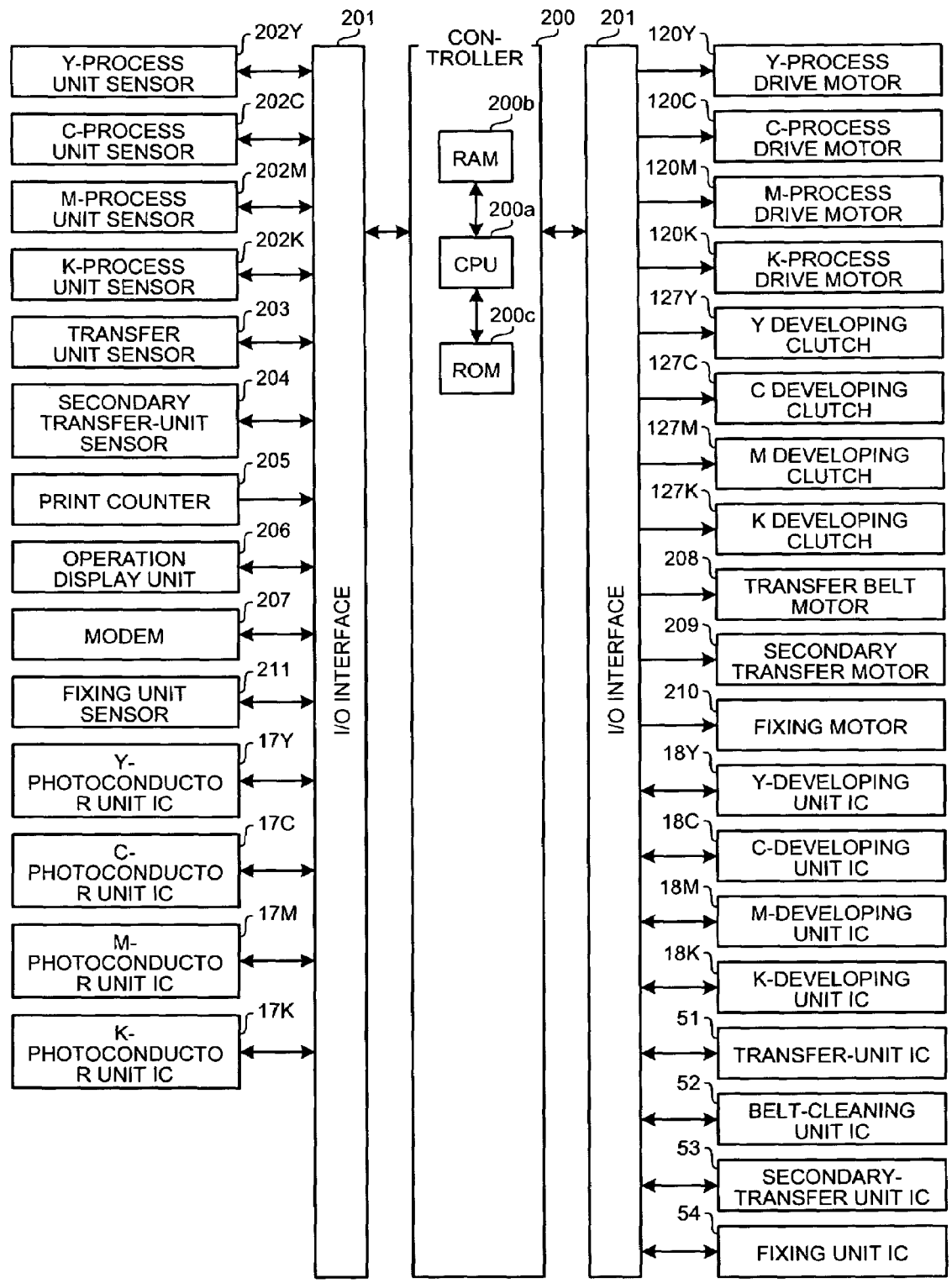
FIG. 14 is a block diagram of one part of an electric circuit in the printer.

The characteristic configuration of the image forming system is explained next. FIG. 14 is a block diagram of a part of an electric circuit in the printer of the image forming system. In FIG. 14, a controller 200 includes a central processing unit (CPU) 200a as a calculation unit, a random access memory (RAM) 200b and a read only memory (ROM) 200c as information storage units. The controller 200 controls the entire printer. A control program for controlling respective units in the printer is stored in the RAM 200b or the ROM 200c, and based on the control program, the units are controlled and various characteristics are ascertained based on an output signal from respective sensors. The process drive motors 120Y, 120C, 120M, and 120K, and the developing clutches 127Y, 127C, 127M, and 127K are connected to the controller 200 via an input/output (I/O) interface 201. Further, process unit sensors 202Y, 202C, 202M, and 202K, a transfer unit sensor 203, a secondary transfer-unit sensor 204, a print counter 205, an operation display unit 206, a modem 207, a transfer belt motor 208, a secondary transfer motor 209, a fixing motor 210, and a fixing unit sensor 211 are also connected to the controller 200.

The process unit sensors 202Y, 202C, 202M, and 202K respectively detect the process units 1Y, 1C, 1M, and 1K set in the printer and output a detection signal to the controller 200.

The transfer unit sensor 203 detects the transfer unit 40 set in the printer and outputs a detection signal to the controller 200.

The secondary transfer-unit sensor 204 detects the secondary transfer unit formed of the secondary transfer roller 50 and the like set in the printer, and outputs a detection signal to the controller 200.

The fixing unit sensor 211 detects the fixing unit 60 set in the printer, and outputs a detection signal to the controller 200.

The print counter 205 counts the accumulated number of prints by the printer immediately after shipment from factory.

The print counter 205 counts up the number of prints every time the printing operation is performed for one sheet of recording paper, and outputs a count-up signal to the controller 200. The print counter 205 outputs a signal indicating the accumulated number of prints to the controller 200 in response to a request from the controller 200.

The operation display unit 206 includes a plurality of key switches and a touch panel (not shown), to convert an input received from the operator through the key switches and the touch panel to an input signal, and output the input signal to the controller 200. Further, the operation display unit 206 displays an image on the touch panel based on a control signal from the controller 200.

The modem 207 transmits a signal received from the controller 200 to a remote apparatus via a telephone line (not shown).

The transfer belt motor 208 is a rotation driving source of the drive roller 47 in the transfer unit 40, and endlessly moves the intermediate transfer belt 41 with the rotation thereof.

The secondary transfer motor 209 is a rotation driving source of the secondary transfer roller 50 that contacts the front surface of the intermediate transfer belt 41 to form the secondary transfer nip. The fixing motor 210 is a rotation driving source of the rollers and the fixing belt in the fixing unit 60.

The controller 200 detects attachment and detachment of the process units 1Y, 1C, 1M, and 1K to and from the printer based on a combination of fall (OFF) and rise (ON) of the output signal from the process unit sensors 202Y, 202C, 202M, and 202K. The controller 200 detects attachment and detachment of the transfer unit 40 to and from the printer based on the combination of fall and rise of the output signal from the transfer unit sensor 203. The controller 200 detects attachment and detachment of the secondary transfer roller 50 to and from the printer based on the combination of fall and rise of the output signal from the secondary transfer-unit sensor 204. Further, the controller 200 detects attachment and detachment of the fixing unit 60 to and from the printer based on the combination of fall and rise of the output signal from the fixing unit sensor 211.

The photoconductor unit ICs 17Y, 17C, 17M, and 17K are integrated circuits (ICs) mounted on an electronic circuit board (not shown) fixed to a unit case as a holding body in photoconductor units 2Y, 2C, 2M, and 2K. The photoconductor unit ICs 17Y, 17C, 17M, and 17K can store information including unit operating time t(i), driven distance D(i), and number of prints P(i) as the operation record of each part in the photoconductor units 2Y, 2C, 2M, and 2K. The photoconductor units 2Y, 2C, 2M, and 2K are detachably mounted on the printer. At the time of attachment or detachment, an electric contact on the electronic circuit board fixed to the unit case is connected to or disconnected from an electric contact on the printer side.

The developing unit ICs 18Y, 18C, 18M, and 18K are integrated circuits (IC) mounted on an electronic circuit board (not shown) fixed to the unit case as the holding body in the developing unit ICs 7Y, 7C, 7M, and 7K. The developing unit ICs 18Y, 18C, 18M, and 18K can store the information including the unit operating time t(i), the driven distance D(i), and the number of prints P(i) as the operation record of each part in the developing units 7Y, 7C, 7M, and 7K. The developing units 7Y, 7C, 7M, and 7K are detachably mounted on the printer. At the time of attachment or detachment, an electric contact on the electronic circuit board fixed to the unit case is connected to or disconnected from an electric contact on the printer side.

A transfer-unit IC 51 is an IC mounted on an electronic circuit board (not shown) fixed to a bracket as the holding body in the transfer unit 40. The transfer-unit IC 51 can store the information including the unit operating time t(i), the driven distance D(i), and the number of prints P(i) as the operation record of each part in the transfer unit 40. The transfer unit 40 is detachably mounted on the printer. At the time of attachment or detachment, an electric contact of the electronic circuit board fixed to the bracket is connected to or disconnected from an electric contact on the printer side. The same applies to a belt-cleaning unit IC 52, a secondary-transfer unit IC 53 and a fixing unit IC 54, and these ICs can store the information such as the unit operating time t(i), the driven distance D(i), and the number of prints P(i) as the operation record of each part in the belt cleaning unit 42, the secondary transfer unit, and the fixing unit 60.

Figure 15:
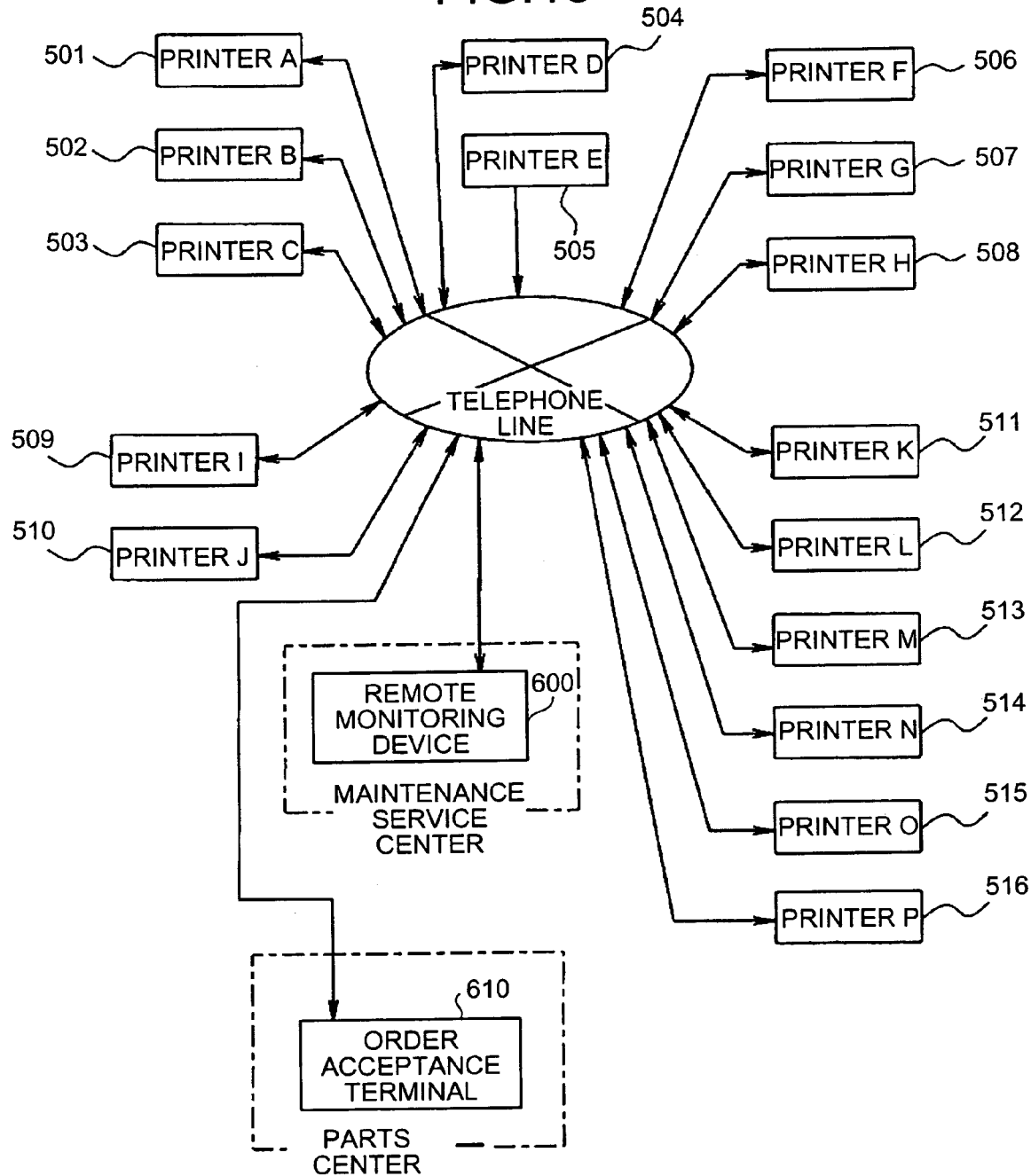
FIG. 15 is one example of the image forming system.

FIG. 15 is one example of the image forming system. The image forming system includes at least one printer installed in the user's site and a lifetime management device (not shown). The image forming system includes 16 printers A to P (501 to 516) installed in different geographical environments. Actually, however, the image forming system often includes several hundreds to several thousands printers. The 16 printers A to P (501 to 516) in respective users are connected to a remote monitoring device 600 in a maintenance service center via the telephone line.

The lifetime management device includes an operation-amount measuring unit that measures the operation amount or operation record of the respective units, i.e., various types of parts or components mounted on the image forming unit of the printer. The lifetime management device also includes a remaining lifetime calculator that calculates remaining lifetime of the respective units based on the operation amount and a predetermined lifetime index. Further, the lifetime management device includes a replacement-request determining unit that determines whether any of the parts need to be replaced based on the remaining lifetime. All the units are arranged in the printer.

In the maintenance service center, technicians highly skilled in failure diagnosis, inspection, and repair of the printer are at work, and a technician is dispatched to each user in response to a request from the user. The printers A to P (501 to 516) include a function referred to as emergency call, and can transmit an emergency call signal including information on a failure content to the remote monitoring device 600 in the maintenance service center via the telephone line. The maintenance service center immediately dispatches the technician upon receiving the emergency call signal by the remote monitoring device 600.

The remote monitoring device 600 in the maintenance service center is connected to an order acceptance terminal 610 of a parts center. In the parts center, various parts of the printers are stocked, and replacement workers who can perform replacement of these parts are at work. The order acceptance terminal 610 in the parts center dispatches a replacement worker to the user together with necessary parts based on a replacement-work request signal transmitted from the remote monitoring device 600 via the telephone line.

In FIG. 15, the image forming system includes the printers, the remote monitoring device 600, and the order acceptance terminal 610, which can communicate with each other via the telephone line as the communication line; however, other communication lines can also be used, including the Internet and a wireless line.

The lifetime management device manages service life information of the photoconductor units 2Y, 2C, 2M, and 2K, the developing units 7Y, 7C, 7M, and 7K, the Y, M, C, and K developers, the transfer unit 40, and the fixing unit 60 in the respective printers as the parts.

The photoconductor units ICs 17Y, 17C, 17M, and 17K, the developing unit ICs 18Y, 18C, 18M, and 18K, the transfer-unit IC 51, the belt-cleaning unit IC 52, the secondary-transfer unit IC 53, and the fixing unit IC 54 are collectively referred to as a unit IC.

Table 1 shows variables of three items stored in the unit ICs.

TABLE 1

| Variable | |
| --- | --- |
| t(i) | Unit operating time [days] |
| D(i) | Driven distance [mm] |
| P(i) | Number of prints [sheets] |

In Table 1, unit operating time t(i) [days] is the operating time of each unit (including developer) after its replacement to the present (elapsed time since replacement), and indicates a characteristic as operation record; driven distance D(i) [mm] is the moving distance of each moving member (rollers and belt) in each unit after its replacement to the present, and also indicates a characteristic as operation record; number of prints P(i) [sheets] is the number of prints produced after replacement of each unit to the present, and also indicates a characteristic as operation record.

Table 2 shows variables of seven items stored in the RAM 200b in the controller 200 of the printer.

TABLE 2

| Variable | |
| --- | --- |
| Ld(i) | Lifetime driven distance [mm] |
| Lp(i) | Lifetime print volume [sheets] |
| T1(i) | Distance remaining lifetime [days] |
| T2(i) | Sheet remaining lifetime [days] |
| T3(i) | Unit remaining lifetime [days] |
| X(i) | Replacement index [days] |
| Y(i) | Order determining added value [days] |

In Table 2, lifetime driven distance Ld(i) [mm] is a lifetime index that is compared to the driven distance D(i) to determine the remaining lifetime of each unit (when the driven distance D(i) reaches the lifetime driven distance Ld(i), the unit is determined to be at the end of its service life); lifetime print volume Lp(i) [sheets] is the number of prints or sheets that can be printed during the lifetime of each unit, i.e., a lifetime index that is compared to the number of prints P(i) to determine the remaining lifetime of each unit (when the number of prints P(i) reaches the lifetime print volume Lp(i), the unit is determined to be at the end of its service life); distance remaining lifetime T1(i) [days] is a remaining lifetime based on a difference between the driven distance D(i) and the lifetime driven distance Ld(i); sheet remaining lifetime T2(i) [days] is a remaining lifetime based on a difference between the number of prints P(i) and the lifetime print volume Lp(i); unit remaining lifetime T3(i) [days] is shorter one of either the distance remaining lifetime T1(i) or the sheet remaining lifetime T2(i); and replacement index X(i) [days] is an index to determine whether to replace each unit.

The variables of three items shown in Table 1 or the variables of seven items shown in Table 2 are individually set for each unit. Lifetime information is managed for the total of 16 units, i.e., the four photoconductor units 2Y, 2C, 2M and 2K, the four developing units 7Y, 7C, 7M and 7K, the Y, M, C, and K developers, the transfer unit 40, the belt cleaning unit 42, the secondary transfer unit, and the fixing unit 60. Accordingly, 144 kinds of variables (nine items ×16) are set. In respective variables, (i) indicates the type of each unit, and the value thereof and the unit type have a relationship shown in Table 3.

TABLE 3

| (i) value | Name |
|---|---|
| 1 | Y photoconductor unit |
| 2 | C photoconductor unit |
| 3 | M photoconductor unit |
| 4 | K photoconductor unit |
| 5 | Y developing unit |
| 6 | C developing unit |
| 7 | M developing unit |
| 8 | K developing unit |
| 9 | Y developer |
| 10 | C developer |
| 11 | M developer |
| 12 | K developer |
| 13 | Transfer unit |
| 14 | Belt cleaning unit |
| 15 | Secondary transfer unit |
| 16 | Fixing unit |

Among the variables of seven items shown in Table 2, distance remaining lifetime $T1(i)$, sheet remaining lifetime $T2(i)$, and unit remaining lifetime $T3(i)$ are unique values for each unit. When the unit is replaced, an eigenvalue of the old unit must be changed to an eigenvalue of the new unit. Therefore, the controller 200 monitors attachment and detachment of the 16 units to and from the printer based on the output value from respective sensors. When attachment or detachment of any unit is detected, the controller 200 performs a replacement inquiry process for the unit. Specifically, when attachment or detachment of, for example, the process unit 1C is detected, the controller 200 inquires of the replacement worker whether the photoconductor unit 2C and the developing unit 7C have been replaced by a screen display on the operation display unit 206. When a response (key input operation) from the replacement worker with respect to the inquiry is Yes for the photoconductor unit 2C, the controller 200 resets the distance remaining lifetime $T1(2)$, the sheet remaining lifetime $T2(2)$ and the unit remaining lifetime $T3(2)$ of the C photoconductor unit, respectively, to predetermined initial values.

The replacement of each unit is not necessarily determined based on the detection of attachment and detachment of the unit and the replacement inquiry process. A unit ID number stored in each unit can be monitored by the controller 200 to determine the replacement of the unit based on a change of the unit ID number.

Further, various variables can be reset by an input operation by the replacement worker who has replaced the unit on the operation display unit 206, instead of the controller 200 ascertaining the replacement of the unit. However, in this case, there is a possibility that the unit life information becomes inappropriate because the replacement worker forgets to perform a reset operation.

The controller 200 performs the following process with respect to each unit (including the developer) at a predetermined time everyday. That is, the controller 200 adds 1 to the unit operating time $t(i)$ stored in the unit IC to update the unit operating time $t(i)$.

The controller 200 updates the driven distances $D(i)$ of the Y, C, M, and K photoconductor units stored in respective unit ICs. Specifically, a time from the start to the end of an operation is counted for the respective process drive motors 120Y, 120C, 120M, and 120K. On completion of time counting, the counting result is multiplied by a predetermined coefficient to convert the photoconductor-unit operating time [sec] to the photosensitive drum-surface moving distance [mm], and the conversion result is added to the driven distances $D(i)$ of the Y, C, M, and K photoconductor units up to that time.

The printer in the image forming system changes over a print speed mode between a high-speed print mode in which respective photosensitive drums, rollers, and belts are driven at a relatively high speed so that priority is given to printing speed rather than image quality, and a low-speed print mode in which respective photosensitive drums and the like are driven at a relatively low speed so that priority is given to the image quality rather than the printing speed. When the photoconductor-unit operating time is converted to the photosensitive drum-surface moving distance, a coefficient corresponding to each mode is used. The coefficient is properly used for other units (the developing unit and the like) in the same manner.

The controller 200 updates the driven distances $D(i)$ of the Y, M, C, and K developing units stored in the respective unit ICs in the following manner. That is, the time from the start of operation to the end of operation is counted for the respective developing clutches 127Y, 127C, 127M, and 127K. On completion of time counting, the counting result is multiplied by a predetermined coefficient to convert the developing unit operating time [sec] to the developing sleeve-surface moving distance [mm], and the conversion result is added to the driven distances $D(i)$ of the Y, C, M, and K developing units up to that time.

Not only the driven distances D(i=5, 6, 7, or 8) of the developing units but also the driven distances D(i=9, 10, 11, or 12) of the developers are stored in the developing unit ICs 18Y, 18C, 18M, and 18K. The driven distances D(i=9, 10, 11, or 12) are updated by employing the surface moving distance (same as that of the developing sleeve) of the transport screw of the developing unit as an alternative characteristic, according to the following manner. That is, the time from the start to the end of the operation is counted for the respective developing clutches 127Y, 127C, 127M, and 127K. On completion of time counting, the counting result is multiplied by a predetermined coefficient to convert the developer operating time [sec] to the surface moving distance [mm] of the transport screw, and the conversion result is added to the driven distances D(i=9 to 12) of the Y, M, C, and K developers up to that time.

The screw and the developing sleeve are turned on/off simultaneously at all times, and the surface migration thereof is synchronized with each other. However, the developing unit and the developer have different driven distance $D(i)$ due to the reason explained below. That is, since the developer has different lifetime from that of the developing unit, in the printer of the image forming system, the replacement cycle of the developer is set to be shorter than that of the developing unit (a threshold described later is different between the developer and the developing unit).

The controller 200 updates the driven distance $D(13)$ of the transfer unit in the following manner. That is, the time from the start to the end of the operation is counted for the transfer belt motor 208. On completion of time counting, the counting result is multiplied by a predetermined coefficient to convert the operating time [sec] of the transfer unit to the surface moving distance [mm] thereof, and the conversion result is added to the driven distance $D(13)$ of the transfer unit up to that time.

The driven distance $D(14)$ of the belt cleaning unit is updated by employing not the moving distance of the cleaning blade 42a itself but the surface moving distance of the intermediate transfer belt 41 contacting the cleaning blade 42a as an alternative characteristic. That is, the time from the start to the end of the operation is counted for the transfer belt motor 208. On completion of time counting, the counting result is multiplied by a predetermined coefficient to convert the blade operating time [sec] to the surface moving distance [mm] of the blade, and the conversion result is added to the driven distance D(14) of the belt cleaning unit up to that time.

The controller 200 updates the driven distance D(15) of the secondary transfer unit in the following manner. That is, the time from the start to the end of the operation is counted for the secondary transfer motor 209. On completion of time counting, the counting result is multiplied by a predetermined coefficient to convert the operating time [sec] of the secondary transfer unit to the moving distance [mm] of the secondary transfer roller, and the conversion result is added to the driven distance D(15) of the secondary transfer unit up to that time.

The controller 200 updates the driven distance D(16) of the fixing unit in the following manner. That is, the time from the start to the end of the operation is counted for the fixing motor 210. On completion of time counting, the counting result is multiplied by a predetermined coefficient to convert the operating time [sec] of the fixing unit to the moving distance [mm] of the fixing belt, and the conversion result is added to the driven distance D(16) of the fixing unit up to that time.

The controller 200 that updates the driven distance D(i) of each unit functions as an operation counting unit that counts the unit operating time, i.e., the operation time of each unit, and converts the unit operating time to the driven distance D(i) as the operation record of the unit.

The number of prints P(i=1 to 16) in each unit is updated by adding 1 to the number of prints P(i=1 to 16) up to that time every time a countup-signal is received from the print counter 205.

The controller 200 that updates the unit operating time t(i), the driven distance D(i), and the number of prints P(i) of respective units functions as an operation-amount measuring unit that measures the unit operating time, which is the operation amount of each unit.

The lifetime driven distance Ld(i=1 to 16) and the replacement index X(i=1 to 16) stored in the controller 200 in each unit has a characteristic as a constant rather than a variable. However, due to some reason, there is a possibility that these can be updated or corrected by a key input by an operator. In the image forming system, therefore, these are handled as variables.

Figure 16:
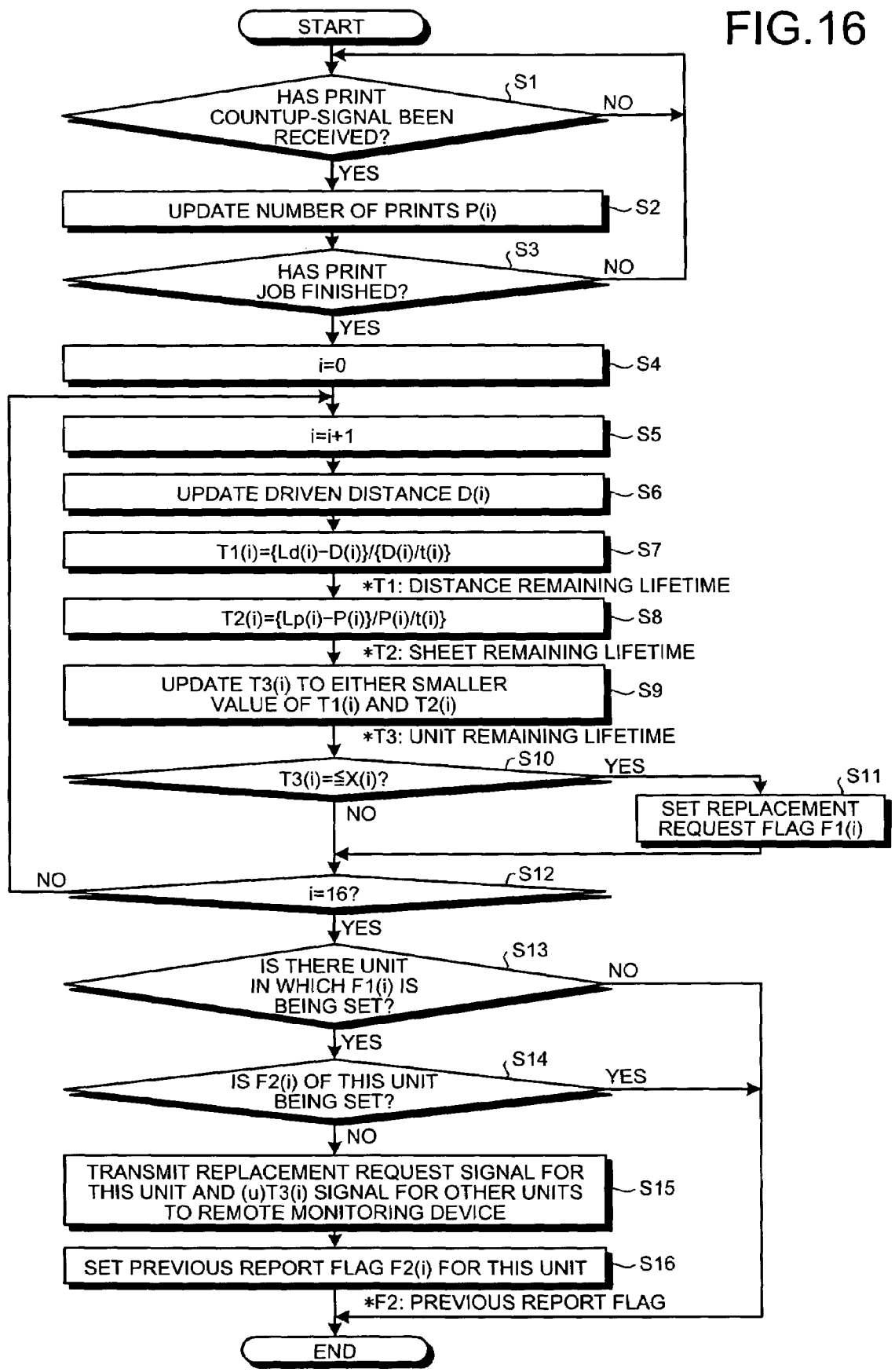
FIG. 16 is a flowchart of a replacement request process performed by a controller in the printer.

FIG. 16 is a flowchart of relevant parts of a replacement request process performed by the controller 200. The replacement request process starts upon start of the print job. When a print countup-signal is output from the print counter 205 (Yes at step S1), the number of prints P(i) stored in the unit IC of the respective units is updated in the above process (step S2). It is then determined whether the print job has finished (step S3). When the print job has not finished (No at step S3), the control flow returns to S1. Accordingly, the number of prints P(i) stored in the unit IC of the respective units is updated for each print job, in a continuous printing operation for continuously printing on a plurality of recording paper.

When the print job has finished (Yes at step S3), after a unit variable i expressing the unit type is reset to zero (step S4), 1 is added to the unit variable i (step S5). The driven distance D(i) stored in the unit IC of the respective units is then updated by the above process (step S6). For example, when the unit variable i is 1, the driven distance D(1) of the Y photosensitive drum stored in the photoconductor unit IC 17Y of the Y photoconductor unit is updated. After the update, the distance remaining lifetime T1(i) is calculated based on the following relational expression (step S7): T1(i)={Ld(i)−D(i)}/{D(i)/t(i)}. The sheet remaining lifetime T2(i) is then calculated based on a relational expression: T2(i)={Lp(i)−P(i)}/{P(i)/t(i)} (step S8), and then the unit remaining lifetime T3(i) is updated to either smaller value of the distance remaining lifetime T1 or the sheet remaining lifetime T2 (step S9).

As is understood from the relational expression shown at step S7, the distance remaining lifetime T1(i) is obtained by dividing a difference between the lifetime driven distance Ld(i) as the assumed lifetime index and the driven distance D(i) up to the present by an average driven distance per day. That is, the distance remaining lifetime T1(i) is a numerical value estimating how many days are required for the driven distance D(i) to reach the lifetime driven distance Ld(i), based on the accumulated driven distances of the unit up to the present. On the other hand, the sheet remaining lifetime T2(i) is, as seen from the relational expression shown at step S8, obtained by dividing a difference between the lifetime print volume Lp(i) as the assumed lifetime index and the number of prints P(i) up to the present by an average number of prints per day. That is, the sheet remaining lifetime T2(i) is a numerical value estimating how many days are required for the number of prints P(i) to reach the lifetime print volume Lp(i), based on the current accumulated number of prints.

While it suffices that only one of the distance remaining lifetime T1(i) and the sheet remaining lifetime T2(i) is calculated and designated as the unit remaining lifetime, in the image forming system, as shown at step S9, the shorter one of T1(i) and T2(i) is designated as the unit remaining lifetime T3(i). This is because of the following reason. That is, the driven distance D(i) and the number of prints P(i) are not in a favorable correlation. Specifically, either in a single printing operation in which an image is formed only on one recording paper or in a continuous printing operation in which images are continuously formed on a plurality of printing paper, an idle operation, in which each unit is driven without forming a toner image, is performed at the time of starting the job and ending the job. The idle operation is performed for the same time period in the single printing operation and the continuous printing operation. Accordingly, in the single printing operation, the percentage of the idle operation time in the total operation time is large, as compared to the continuous printing operation. Further, in the continuous printing operation, the percentage of the idle operation changes according to the number of continuous printing, and as the number of continuous printing increases, the percentage of the idle operation time decreases. Therefore, in a user who performs the single printing operation relatively frequently, the driven distance D(i) relatively increases, although the number of prints by parts P(i) is relatively small. With such a user, if the unit remaining lifetime is determined based on only the number of prints by parts P(i), there is a possibility that the parts can be worn out before life estimation is performed. On the contrary, in a user who performs the continuous printing operation relatively frequently, the number of prints by parts P(i) relatively increases, although the driven distance D(i) is relatively short. With such a user, if the unit remaining lifetime is determined based on only the driven distance D(i), there is a possibility that the parts can be worn out before life estimation is performed. Therefore, in the image forming system, either smaller value of the driven distance D(i) or the number of prints P(i) is designated as the unit remaining lifetime T3(i). Accordingly, unit life estimation can be accurately performed both for the user who performs the single printing operation relatively frequently and the user who performs the continuous printing operation relatively frequently.

The controller 200 that updates the unit remaining lifetime T3(i) in this manner functions as a remaining lifetime calculator that calculates the distance remaining lifetime T1 of each unit based on the unit operating time t(i) and the driven distance D(i), which is the operation record by parts, and the lifetime driven distance Ld(i) as the lifetime index. The controller 200 also functions as a remaining lifetime calculator that calculates the sheet remaining lifetime T2 of each unit as the parts, based on the unit operating time t(i) and the number of prints P(i), which is the operating amount by parts, and the lifetime print volume Lp(i) as the lifetime index.

When the unit remaining lifetime T3(i) is updated, it is then determined whether the unit remaining lifetime T3(i) has reached a predetermined replacement index X(i) (step S10). If the replacement index X(i) is set, for example, to 45 [days], it is determined that "the unit will wear out soon" 45 days prior to the day when the unit is estimated to wear out. If such a determination is not made (No at step S10), in other words, when it is determined that there is enough time until the service life of the unit ends, it is then determined whether the unit variable i is 16, that is, life estimation has been performed with respect to all types of units (step S12). When the unit variable i is not 16 (No at step S12), the control flow returns to S5. Accordingly, life estimation is performed for the next unit.

On the other hand, at step S11, if it is determined that "the unit will wear out soon" (Yes at step S10), after a replacement request flag F1(i) is set for the unit (step S1), the step S12 is performed.

Thereafter, when it is determined that the unit variable i is 16 at step S12, that is, when life estimation has been performed with respect to all types of units, it is then determined whether any one of the replacement request flags F1(1) to F1(16) is being set (step S13). When it is determined that no replacement request flag is being set (No at step S13), the continuous control flow finishes. On the other hand, when it is determined that a replacement request flag is being set (Yes at step S13), it is determined whether a previous report flag F2(i) is being set for the unit (step S14).

The previous report flag F2(i) is set when the unit corresponding to the unit variable i transmits a replacement request signal indicating that replacement is necessary to the remote monitoring device 600, and released when the replacement of the unit is made. When there is a unit with the previous report flag F2(i) being set (Yes at step S14), the replacement request signal was transmitted for the unit in the past. Therefore, the continuous control flow finishes without transmitting the replacement request signal for the unit. On the other hand, when the previous report flag F2(i) is not set for all the units (No at step S14), the replacement request signal for the unit, for which replacement of the unit is required, and a signal of the unit remaining lifetime (u)T3(i) for all other units are transmitted from the modem 207 as a transmitter to the remote monitoring device via the telephone line (step S15). After the previous report flag F2(i) is set for the unit (step S16), the continuous control flow finishes. The reason why the unit remaining lifetime is expressed as (u)T3(i) instead of T3(i) is that not only the information on the unit remaining lifetime but also an individual user ID (or printer ID) added to each user are transmitted at the same time at step S15. The sign "u" expresses the user ID. Since the user ID information is transmitted at the same time, the remote monitoring device having received the signal can specify in which unit of which user the replacement request has been issued.

The controller 200 that performs such a replacement request process functions as a replacement-request determining unit that determines whether replacement of each unit is necessary based on the calculation result by the remaining lifetime calculator, and the distance remaining lifetime T1(i) and the sheet remaining lifetime T2(i) as predetermined replacement indices.

Figure 17:
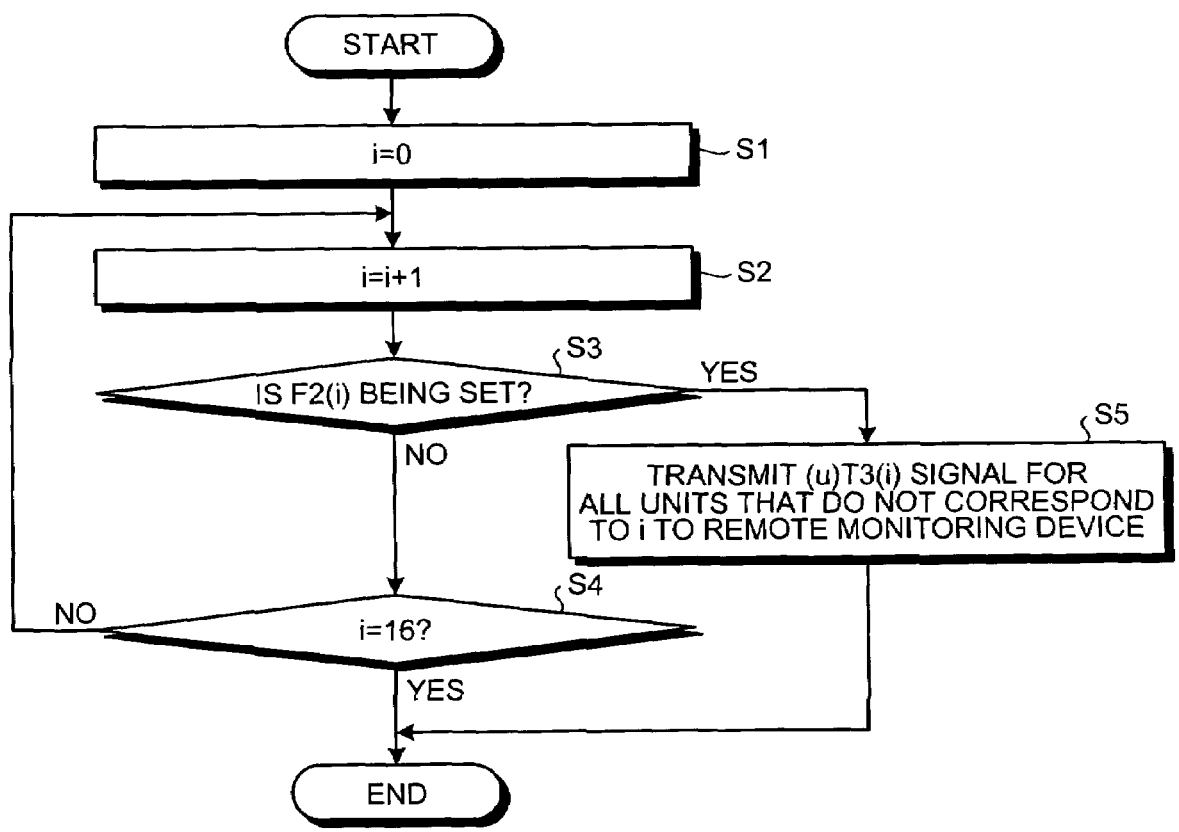
FIG. 17 is a flowchart of relevant parts of a remaining lifetime informing process performed by the controller.

FIG. 17 is a flowchart of relevant parts of a remaining lifetime informing process performed by the controller 200. The remaining lifetime informing process is performed everyday at a predetermined time. When the remaining lifetime informing process is started, the unit variable i is reset to zero (step S1), and 1 is added to the unit variable i (step S2). It is then determined whether the previous report flag F2(i) is being set (step S3). When the previous report flag F2(i) is being set, the replacement request has already been issued in the unit corresponding to the unit variable i, and the replacement request signal for the unit has been already transmitted to the remote monitoring device. In such a case (Yes at step S3), a signal of the unit remaining lifetime (u)T3(i) for all the units not corresponding to the unit variable i is transmitted to the remote monitoring device (step S5). Thus, when a replace request is issued in any unit, the unit remaining lifetime (u)T3(i) of all other units is regularly transmitted to the remote monitoring device everyday at step S5, until the replacement work of the unit is completed.

When it is determined that the previous report flag F2(i) is not being set (No at step S3), it is then determined whether the unit variable i is 16, and when the unit variable i is not 16, the control flow returns to S2. It is then determined whether the previous report flag F2(i+1) is being set for the next unit (i+1).

The remote monitoring device 600 installed in the maintenance service center has a modem as a communication unit, a CPU as a calculation unit, a display as a screen display unit, and an RAM, an ROM, and a hard disk as information storage units. When a signal transmitted from respective printers via the telephone line is received by the modem as the communication unit, various types of data processes are performed based on the signal.

Figure 18:
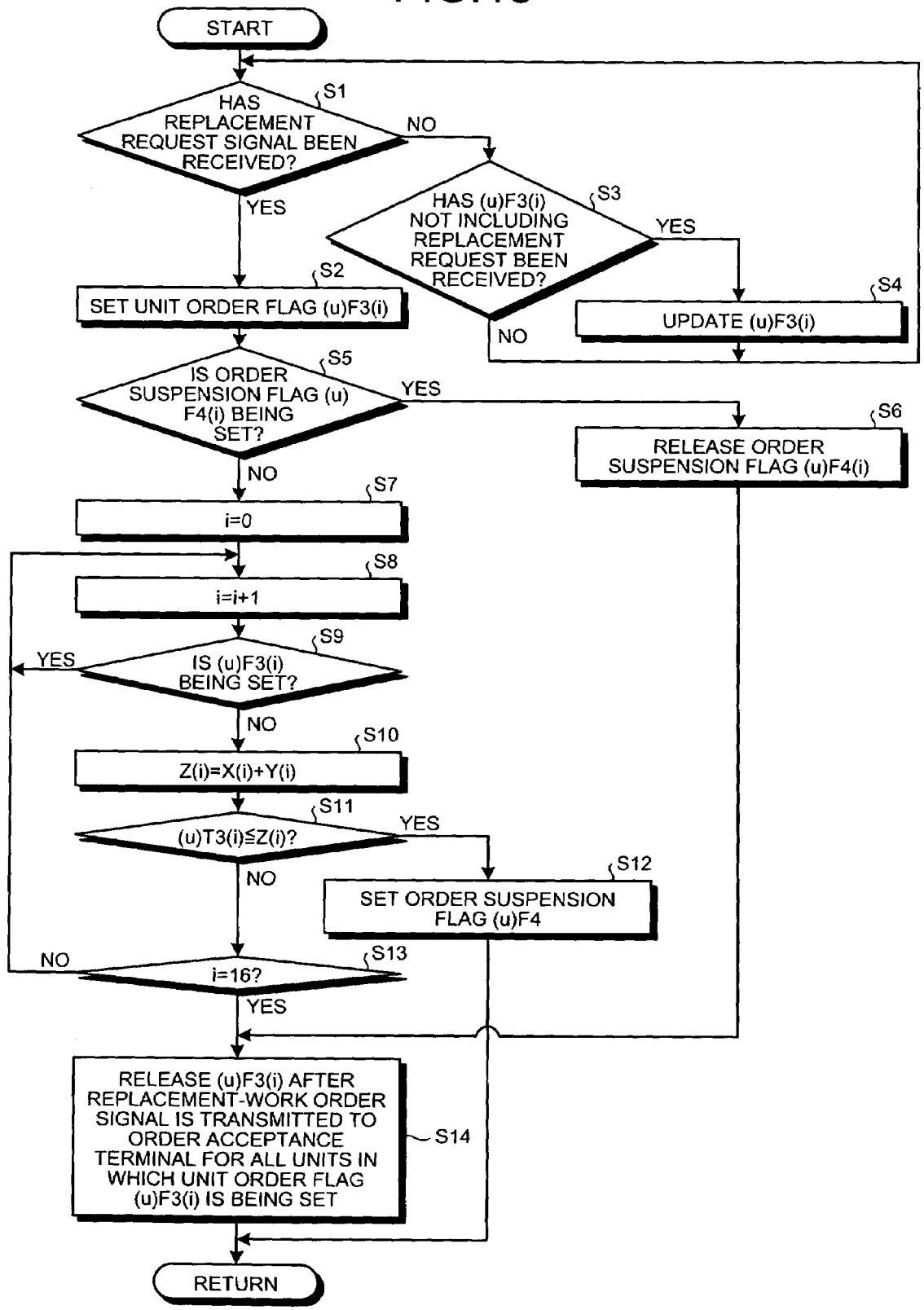
FIG. 18 is a flowchart of relevant parts of a replacement order process performed by a remote monitoring device in the image forming system.

FIG. 18 is a flowchart of relevant parts of a replacement order process performed by the remote monitoring device 600. When a replacement request signal is received from any printer connected to the remote monitoring device 600 via the telephone line (Yes at step S1), a unit order flag (u)F3(i) for the unit in the printer (user) is set (step S2). It is then determined in the subsequent process that it is necessary to order the replacement work of the unit corresponding to the unit variable i in the printer (u), according to the setting of the unit order flag (u)F3(i).

Further, when a signal of the unit remaining lifetime (u)T3(i), which does not include the replacement request signal from some printer connected to the remote monitoring device 600 via the telephone line, is received (Yes step S3), the unit remaining lifetime (u)T3(i) already stored in the hard disk is replaced by a new one (step S4). Accordingly, the unit remaining lifetime (u)T3(i) for other units regularly transmitted everyday from the printer, in which the replacement request has is issued for some unit, is regularly updated everyday in the remote monitoring device.

Thereafter, steps S5 and S6 are performed (these are explained later) for easier understanding. Steps S7 to S13 forms a step group, at which various kinds of determination processes are performed for units, for which the unit order flag (u)F3(i) is not set at step S2, in other words, units in which the replacement request has not yet been issued.

At the step group of steps S7 to S13, at first, after the unit variable i is reset to zero (step S7), 1 is added to the unit variable i (step S8). It is then determined whether the unit order flag (u)F3(i) corresponding to the unit variable i is being set (step S9). Due to a reason described below, when it is determined that the unit order flag (u)F3(i) is being set (Yes at step S9), the unit variable i at that time corresponds to the unit for which the unit order flag (u)F3(i) has been set at step S2. In such a case, the control flow returns to S8, and 1 is added to the unit variable i to perform determination for the next unit.

On the other hand, when the unit order flag (u)F3(i) is not set (No at step S9), an order determination threshold Z(i) is set to a value obtained by adding an order determining additional value Y(i) to the replacement index X(i) (step S10). The order determination threshold Z(i) is a threshold for determining the necessity of order for replacement work, and is set in unit of day for each type of unit. The replacement index X(i) is the same as the one used in the replacement request process shown in FIG. 16. As explained above, the replacement index X(i) is for determining whether the unit remaining lifetime T3(i) is within a predetermined time. For example, in the case of a unit in which it is desired to issue a replacement request 45 [days] prior to the day when the unit is estimated to wear out, the replacement index X(i) is set to 45 days. On the other hand, the order determining additional value Y(i) indicates time [days] up to a point in time dated back slightly from a point in time when it is desired to issue a replacement request. The replacement request is issued at a point in time dated back by the replacement index X(i) from the day when the unit is estimated to wear out, however, the order determination threshold Z(i) is set to Z(i)=X(i)+Y(i) to determine whether the requirement for issuing the replacement request is satisfied (whether the unit remaining lifetime is within the range) even if the replacement index X(i) is extended slightly longer. At the next step S11, it is determined whether the unit remaining lifetime (u)T3(i) is equal to or less than the order determination threshold Z(i).

When the unit remaining lifetime (u)T3(i) is longer than the order determination threshold Z(i) (No at step S11), it means that the replacement request is not issued even if the replacement index X(i) is extended slightly longer than the original value. In such a case, the determination process for the unit corresponding to the unit variable i finishes (No at step S13), and the determination process for the next unit corresponding to the unit variable i is performed (steps S8 to S11). On the other hand, when the unit remaining lifetime (u)T3(i) is equal to or less than the order determination threshold Z(i) (Yes at step S11), it means that the replacement request is issued if the replacement index X(i) is extended slightly longer than the original value. In such a case, after an order suspension flag (u)F4 corresponding to the user variable u is set (step S12), the continuous control flow returns to the initial step. The order suspension flag (u)F4(i) is a flag for suspending the order of replacement work with respect to the unit in which the unit order flag (u)F3(i) is set.

In other words, in the step group of steps S7 to S13, it is determined whether the requirement for issuing the replacement request is satisfied when the replacement index X(i) is extended slightly longer than the original value, with respect to units other than the unit in which the replacement request has been already issued. When the requirement is satisfied in some unit, the order suspension flag u)F4(i) is set therein, and the order of replacement work with respect to the unit in which the replacement request has been already issued is suspended. At this time, the unit order flag (u)F3(i) for the unit in which the replacement request has been already issued is remained in the set state (step S2).

On the other hand, when the requirement for issuing the replacement request is not satisfied even if the replacement index X(i) is extended slightly longer than the original value, in all the units other than the unit in which the replacement request has been already issued (Yes at step S13), the replacement work is ordered for the unit. Specifically, a replacement-work order signal for the unit in which the replacement request has been already issued is transmitted to the order acceptance terminal 610 in the parts center from the modem of the remote monitoring device via the telephone line (step S14). Accordingly, a replacement worker is dispatched from the parts center to the user to replace the unit in which the replacement request has been issued. Upon transmission of the replacement-work order signal, all the unit order flags (u)F3(i) being set are released.

As explained above, when the replacement request signal transmitted from the user printer is received at step S1, the unit order flag (u)F3(i) is set for the unit of the user, in which the replacement request has been issued (step S2). It is then determined whether the order suspension flag (u)F4(i) is being set (step S5). When the order suspension flag (u)F4(i) is being set, a replacement request issued in the past in a unit other than the unit in which the unit order flag (u)F3(i) has been set at step S2 immediately before, and the unit order flag (u)F3(i) has been already set as well for the unit. However, the replacement work for that unit is suspended due to setting of the order suspension flag (u)F4(i), and hence the order has not been placed yet. In other words, when it is determined that the order suspension flag (u)F4(i) is being set at step S5, the condition is as described below. That is, although a replacement request issued in the past for a certain unit, it was estimated that a replacement request for another unit separate from the unit would be issued soon, and hence the order of the replacement work for the former unit was suspended and then the replacement request for the latter unit had just been issued. Therefore, in such a case (Yes at step S5), after the order suspension flag (u)F4(i) is released (step S6), a replacement-work order signal for these units is transmitted to the order acceptance terminal in the parts center.

The control flows shown in FIGS. 16, 17, and 18 can be consolidated as follows. That is, when a replacement request has been issued in some unit, a replacement request signal for the unit and the unit remaining lifetime (u)T3(i) for other units are transmitted to the remote monitoring device 600 in the maintenance service center. Thereafter, the printer continuously transmits the unit remaining lifetime (u)T3(i) for all other units regularly everyday to the remote monitoring device 600, until the replacement of the unit in which replacement request been issued has finished. On the other hand, upon receiving the unit remaining lifetime (u)T3(i) transmitted regularly everyday from some printer, the remote monitoring device 600 sequentially updates the unit remaining lifetime (u)T3(i). Upon reception of a replacement request signal transmitted from some printer, the remote monitoring device 600 determines whether the order suspension flag (u)F4 is being set for the printer. When the order suspension flag (u)F4 is not set, that is, if there is no other unit, whose replacement work is suspended in the printer, the remote monitoring device 600 determines whether a replacement request will be issued soon in the units in which the replacement request has not been issued yet at present. If there is a unit in which the replacement request will be issued soon, the order of replacement work for the unit in which the replacement request has already been issued is temporary suspended. If there is no unit in which the replacement request will be issued soon, the replacement work of the unit in which the replacement request has already been issued is ordered immediately. Having received the replacement request signal, when the remote monitoring device 600 determines that the order suspension flag (u)F4 is being set, the remote monitoring device 600 concurrently orders the replacement work of the unit corresponding to the replacement request signal received immediately before, and the replacement work of another unit, for which the order of replacement work was suspended in the past. Accordingly, since the replacement work of two units in which the replacement request is issued in a relatively short period is ordered concurrently, maintenance work can be performed more efficiently than before.

In the image forming system having such a configuration, it is assumed that a secondhand part is used instead of a new one as the replacement parts of any unit mounted on the printer. Even in this case, the unit operating time t(i), the driven distance D(i), and the number of prints P(i) up to that time of the secondhand unit can be obtained from the unit IC as the operation-information storage unit provided in the unit case as the holding body of the unit. Accordingly, life estimation of the secondhand unit can be accurately performed by calculating the unit remaining lifetime T3($i$) based on the unit operating time t(i), the driven distance D(i), and the number of prints P(i).

Figure 19:
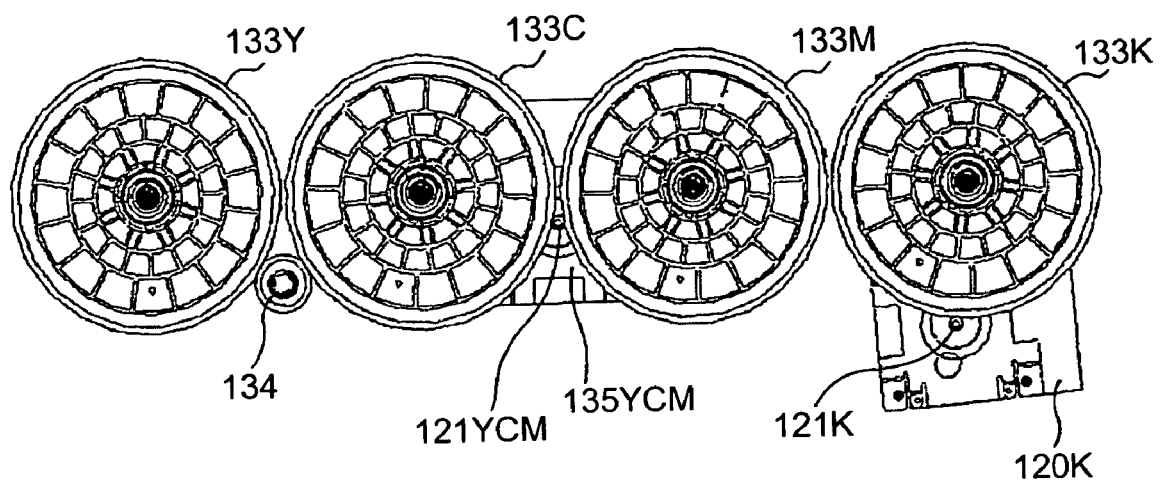
FIG. 19 is an enlarged view of four photoconductor gears and a peripheral configuration thereof in a printer of an image forming system according to a modification of the embodiment.

A modified example of the image forming system of the embodiment is explained next. The modified example has the same configuration as previously described unless otherwise specified. FIG. 19 is an enlarged view of four photoconductor gears 133Y, 133C, 133M, and 133K, and a peripheral configuration thereof in a printer of an image forming system according to a modification of the embodiment. The Y, C, and M photosensitive drums in the printer are driven by a photoconductor drive motor exclusive for the photoconductor units, instead of using a process drive motor, which also functions as a drive source of the photoconductor units and a drive source of the developing units. Further, the three Y, C, and M photoconductor units are driven by one photoconductor drive motor 135YCM, instead of being driven by each exclusive photoconductor drive motor. A drive gear 121YCM fixed to a motor shaft of the photoconductor drive motor 135YCM engages with the photoconductor gear 133C and the photoconductor gear 133M. Accordingly, the Y photosensitive drum and the M photosensitive drum are rotated.

The photoconductor gear 133C engages with the photoconductor gear 133Y via an idler gear 134. Accordingly, the Y photosensitive drum is rotated via the drive gear 121YCM, the photoconductor gear 133C, the idler gear 134, and the photoconductor gear 133Y.

On the other hand, the K photoconductor unit and the K developing unit are driven by the process drive motor 120K as in the image forming system according to the embodiment. The drive gear 121K fixed to the motor shaft of the process drive motor 120K engages with the photoconductor gear 133K. Accordingly, the K photosensitive drum is rotated. Although not shown for brevity, the drive gear 121K also engages with the developing gear (not shown), and a rotation driving force of the developing gear is transmitted to the developing unit via the developing clutch (not shown).

The Y, M, and C developing units (not shown) are driven by one developing motor (not shown) that commonly drives these developing units.

In the printer having such a configuration, the driven distances D(i=1 to 3) of the Y, C, and M photoconductor units are calculated, respectively, based on the operating time of the one photoconductor drive motor 135YCM. However, since there is a possibility that one or two photoconductor units of the Y, C, and M three photoconductor units can be unexpectedly replaced due to a failure or the like, the driven distances D(i=1 to 3) of the photoconductor units are calculated separately for each color. The number of prints of the Y, C, and M photoconductor units P(i=1 to 3) is also calculated separately for each color of Y, C, and M, due to the same reason.

The driven distances D(i=5 to 7) of the Y, C, and M developing units, and the driven distances D(i=9 to 11) of the Y, C, and M developers are calculated based on the operating time of one developing motor. However, since there is a possibility that one or two developing units of the Y, C, and M three developing units can be unexpectedly replaced due to a failure or the like, the driven distances of the developing units and the driven distances of the developers are calculated separately for each color. The number of prints of the developing units P(i=5 to 7) is also calculated separately for each color of Y, C, and M, due to the same reason.

The driven distance D(4) of the K photoconductor unit, the driven distance D(8) of the K developing unit, and the driven distance D(12) of the K developer are calculated by the same process as in the embodiment.

While the image forming system including the image forming unit that forms color images by the process units for different colors has been explained, the present invention is also applicable to an image forming system with an image forming apparatus that forms only monochrome images.

As described above, according to the embodiment, the controller 200 measures the number of prints P(i), i.e., the number of recording paper sheets on which an image is formed by the image forming unit that includes various types of parts, with respect to each part. Thus, the controller 200 can calculate the sheet remaining lifetime T2($i$) based on the number of prints P(i).

The image forming unit includes photosensitive drums 3Y, 3C, 3M, and 3K as latent image carriers each carrying a latent image on the endlessly moving surface, a developing sleeve as a developing member that obtains a visible image by developing the latent image with a developer carried on the endlessly moving surface, the transfer unit 40 that transfers a toner image being the visible image onto the intermediate transfer belt 41 with an endlessly moving surface, and the fixing belt 64 that fixes the toner image on the recording paper P. The controller 200 measures the number of prints P(i) with respect to the photosensitive drums, the developing sleeve, the intermediate transfer belt 41, and the fixing belt 64, respectively. Thus, the controller 200 can calculate the sheet remaining lifetime T2($i$) of the photosensitive drums, the developing sleeve, the intermediate transfer belt 41, and the fixing belt 64, respectively.

The controller 200 measures the driven distance D(i), i.e., the accumulated surface moving distance, in addition to the number of prints P(i), as the operation record, of the photosensitive drums, the developing sleeve, the intermediate transfer belt 41, and the fixing belt 64. Thus, the controller 200 can calculate the unit remaining lifetime T3($i$) more accurately, compared to a case that the controller 200 calculates the unit remaining lifetime T3($i$) based only on the number of prints P(i).

The cleaning blade 42a cleans the surface of the intermediate transfer belt 41 while contacting the surface thereof, and the controller 200 measures the driven distance D(13) of the intermediate transfer belt 41 as an alternative of the driven distance D(14) of the cleaning blade 42a. Thus, wear of the cleaning blade 42a, which is a part whose surface is not endlessly moved, is determined based on the driven distance D(13) of the transfer unit, i.e., the surface moving distance of the intermediate transfer belt 41 contacting the cleaning blade 42a. The unit remaining lifetime T3($i$) of the cleaning blade 42a (the cleaning unit) can thereby be accurately estimated.

The controller 200 measures the unit operating time t(i), i.e., the accumulated operating time of the photosensitive drums, the developing sleeve, the intermediate transfer belt 41 and the fixing belt 64, in addition to the number of prints P(i) and the driven distance D(i) as the operation record. Thus, the controller 200 can calculate the unit remaining lifetime T3(i) more accurately, compared to a case that the controller 200 calculates the unit remaining lifetime T3(i) based only on the number of prints P(i), on the driven distance D(i), or based only on the both.

The printer can be configured to transmit the measurement results of the unit operating time t(i), the number of prints P(i), and the driven distance D(i) to the remote monitoring device 600 located at a remote site via a communication line such as a telephone line. The remote monitoring device 600 can be configured to calculate the unit remaining lifetime T3(i) based on the measurement results or determine the necessity of the replacement request. In other words, a remaining lifetime calculator and a replacement-request determining unit can be provided in the remote monitoring device 600 as an information processor, instead of being provided in the printer. In this case, the configuration of each printer can be simplified, which enables a reduction in the cost of each printer.

The controller 200 functions as a remaining lifetime calculator that calculates the unit remaining lifetime T3(i) of respective units based on the operation amount thereof and a predetermined lifetime index. Thus, the unit remaining lifetime T3 can be calculated in the user who has the printer installed therein.

The controller 200, which is a part of the lifetime management device, is configured as a replacement-request determining unit that determines whether each unit needs to be replaced based on the unit remaining lifetime T3(i). Therefore, the user can be automatically informed that the replacement work of each unit is required at an appropriate timing before the respective units wear out.

The modem 207 functions as a transmission unit that transmits determination results obtained by the controller 200 to the remote monitoring device 600 located at a remote site via a telephone line as a communication line. Thus, a maintenance service organization at a remote site can be automatically informed that the replacement work is required at an appropriate timing before the respective units wear out.

As set forth hereinabove, according to an embodiment of the present invention, each part of an image forming unit or a holder that holds the part includes a storage unit that stores the operation amount of the part up to that time. Therefore, even when a secondhand part is used as a renewal part of the image forming unit, the operation amount of the secondhand part is obtained based on a period from when the part was new to the present. That is, the operation amount before a part was detached from an image forming unit and that since the part was mounted again as a secondhand part on another image forming unit can be correctly measured. With the operation amount measured in this manner, the remaining lifetime of the secondhand part can be accurately estimated. Thus, it is possible to accurately calculate the end of service life of even a secondhand part.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. An image forming apparatus, comprising:
an image forming unit that forms an image on a recording medium, including:
a latent image carrier that carries a latent image on a surface of a transfer belt;
a developing unit that develops the latent image on the latent image carrier to a visible image with a developer carried on the transfer belt;
a transfer unit that transfers the visible image on the latent image carrier onto any one of the transfer belt and a recording medium on a surface of the transfer belt;
a fixing unit that fixes the visible image on the recording medium; and
a cleaning unit that cleans the surface of the transfer belt while contacting thereof, and
a measuring unit that measures an operation amount of at least one of the latent image carrier, the developing unit, the the transfer unit, the fixing unit, and the cleaning unit, wherein
any one of the latent image carrier, the developing unit, the transfer unit, the fixing unit, the cleaning unit, and a holding unit, respectively, includes a storage unit that stores therein operation amount information on the operation amount obtained by the measuring unit,
the measuring unit updates the operation amount information after measuring the operation amount, and
the measuring unit measures an accumulated moving distance of at least one of the latent image carrier, the developing unit, the transfer belt, and the fixing unit as an alternative of an accumulated moving distance of the cleaning unit.

2. The image forming apparatus according to claim 1, wherein the measuring unit counts number of recording media on which an image is formed by the image forming unit as the operation amount.

3. The image forming apparatus according to claim 1, wherein:
the measuring unit measures the operation amount of at least two of the latent image carrier, the developing unit, the transfer belt, and the fixing unit.

4. The image forming apparatus according to claim 1, wherein the measuring unit further measures an accumulated operating time of at least one of the latent image carrier, the developing unit, the transfer belt, the fixing unit, and the cleaning unit as the operation amount.

5. The image forming apparatus according to claim 1 further comprising a transmitting unit that transmits the operation amount information to an information managing apparatus located at a remote place via a communication line.

6. The image forming apparatus according to claim 1 further comprising a calculating unit that calculates a remaining lifetime of the component based on the operation amount.

7. An image forming system, comprising:
an image forming unit that forms an image on a recording medium, including:
a latent image carrier that carries a latent image on a surface of a transfer belt;
a developing unit that develops the latent image on the latent image carrier to a visible image with a developer carried on the transfer belt;
a transfer unit that transfers the visible image on the latent image carrier onto any one of the transfer belt and a recording medium on a surface of the transfer belt;

a fixing unit that fixes the visible image on the recording medium; and a cleaning unit that cleans the surface of the transfer belt while contacting thereof, and a lifetime management unit including:

a measuring unit that measures an operation amount of at least one of the latent image carrier, the developing unit, the transfer unit, the fixing unit, and the cleaning unit, and a calculating unit that calculates a remaining lifetime of the latent image carrier, the developing unit, the transfer unit, the fixing unit and the cleaning unit based on the operation amount and-a lifetime index, wherein any one of the latent image carrier, the developing unit, the transfer unit, the fixing unit, and the cleaning unit and a holding unit, respectively, includes a storage unit that stores therein operation amount information on the operation amount obtained by the measuring unit, the measuring unit updates the operation amount information after measuring the operation amount, and the measuring unit measures an accumulated moving distance of at least one of the latent image carrier, the developing unit, the transfer belt, and the fixing unit as an alternative of an accumulated moving distance of the cleaning unit.

8. The image forming system according to claim 7, wherein the lifetime management unit further includes a determining unit that determines whether at least one of the latent image carrier, the developing unit, the transfer belt, the fixing unit, and the cleaning unit needs to be replaced based on the remaining lifetime.

9. The image forming system according to claim 8 further comprising an informing unit that informs an information managing apparatus located at a remote place of a determination result obtained by the determining unit via a communication line.

10. The image forming apparatus according to claim 1, wherein the measuring unit measures the accumulated moving distance of the transfer belt as an alternative of the accumulated moving distance of the cleaning unit.

11. The image forming apparatus according to claim 7, wherein the measuring unit measures the accumulated moving distance of the transfer belt as an alternative of the accumulated moving distance of the cleaning unit.

12. An image forming apparatus, comprising:

an image forming unit that forms an image on a recording medium, including:

a latent image carrier that carries a latent image on a surface of a transfer belt;

a developing unit that develops the latent image on the latent image carrier to a visible image with a developer carried on the transfer belt;

a transfer unit that transfers the visible image on the latent image carrier onto any one of the transfer belt and a recording medium on a surface of the transfer belt;

a fixing unit that fixes the visible image on the recording medium; and a cleaning unit that cleans the surface of the transfer belt while contacting thereof, and a measuring unit that measures an operation amount of at least one of the latent image carrier, the developing unit, the the transfer unit, the fixing unit, and the cleaning unit, wherein any one of the latent image carrier, the developing unit, the transfer unit, the fixing unit, the cleaning unit, and a holding unit, respectively, includes a storage unit that stores therein operation amount information on the operation amount obtained by the measuring unit, the measuring unit updates the operation amount information after measuring the operation amount, the measuring unit measures an accumulated moving distance of at least one of the latent image carrier, the developing unit, the transfer belt, and the fixing unit as an alternative of an accumulated moving distance of the cleaning unit, and the measuring unit counts number of recording media on which an image is formed by the image forming unit as the operation amount.

* * * * *